(12) United States Patent
Cook et al.

(10) Patent No.: US 6,952,649 B2
(45) Date of Patent: Oct. 4, 2005

(54) PETROLEUM EXPLORATION AND PREDICTION APPARATUS AND METHOD

(76) Inventors: Daniel R. Cook, 3323 S. Davis Blvd., Bountiful, UT (US) 84010; John D. Walther, 1218 Pioneer Dr., Richmond, TX (US) 77469

(*) Notice: Subject to any disclaimer, the term of this patent is extended or adjusted under 35 U.S.C. 154(b) by 20 days.

(21) Appl. No.: 10/676,945

(22) Filed: Oct. 1, 2003

(65) Prior Publication Data
US 2004/0068375 A1 Apr. 8, 2004

Related U.S. Application Data

(63) Continuation-in-part of application No. 10/364,785, filed on Feb. 11, 2003, now Pat. No. 6,745,156.
(60) Provisional application No. 60/416,342, filed on Oct. 4, 2002.

(51) Int. Cl.$^7$ ................................................. G01V 1/28
(52) U.S. Cl. ......................................... 702/14; 702/13
(58) Field of Search .............................. 702/10–14, 16, 702/17, 18; 367/73

(56) References Cited

U.S. PATENT DOCUMENTS

| | | | | |
|---|---|---|---|---|
| 4,883,067 A | 11/1989 | Knispel et al. | ............. | 128/732 |
| 5,213,338 A | 5/1993 | Brotz | ............. | 273/460 |
| 5,222,210 A | 6/1993 | Leivian | ............. | 395/161 |
| 5,253,332 A | 10/1993 | Kumamoto | ............. | 395/51 |
| 5,255,347 A | 10/1993 | Matsuba et al. | ............. | 395/23 |
| 5,299,118 A | 3/1994 | Martens et al. | ............. | 364/413.05 |
| 5,353,380 A | 10/1994 | Zhang | ............. | 395/3 |
| 5,355,435 A | 10/1994 | DeYong et al. | ............. | 395/24 |
| 5,377,100 A | 12/1994 | Pope et al. | ............. | 364/410 |
| 5,379,268 A | 1/1995 | Hutson | ............. | 367/100 |
| 5,392,210 A | 2/1995 | Scholz | ............. | 364/413.01 |
| 5,392,788 A | 2/1995 | Hudspeth | ............. | 128/731 |
| 5,402,521 A | 3/1995 | Niida et al. | ............. | 395/22 |
| 5,406,957 A | 4/1995 | Tansey | ............. | 128/732 |

(Continued)

FOREIGN PATENT DOCUMENTS

| | | |
|---|---|---|
| EP | 743217 | 11/1996 |
| EP | 745843 | 12/1996 |
| WO | WO 96/38726 | 12/1996 |

OTHER PUBLICATIONS

J.J. Rajan and P.J.W. Rayner, "Time Series Classification Using the Volterra Connectionist Model and Bayes Decision Theory," IEEE Int'l. Conf. on Acoustics, Speech and Signal Processing, vol. 1, pp. 601–604.

(Continued)

*Primary Examiner*—Donald McElheny, Jr.
(74) *Attorney, Agent, or Firm*—Pate Pierce & Baird

(57) ABSTRACT

A method for predicting the state of a geological formation. The method may include generating a separation key effective to extract a first feature from a signal or signals corresponding to a first state and a second feature, distinct from the first feature, from a signal or signals corresponding to a second state. The separation key may list at least one feature operator and a weighting table. The at least one feature operator may expand a test signal collected from a geological formation of unknown state in at least one of frequency space and time space to generate a plurality of feature segments. A weighting table may weight the plurality of feature segments. The weighted plurality of feature segments may be superimposed to form a third feature. The geological formation may be classified as having one of the first state and second state based on the correspondence of the third feature to one of the first feature and second feature.

41 Claims, 28 Drawing Sheets

U.S. PATENT DOCUMENTS

| | | | |
|---|---|---|---|
| 5,434,955 A | 7/1995 | Kumamoto | 395/51 |
| 5,444,619 A | 8/1995 | Hoskins et al. | 364/421 |
| 5,447,166 A | 9/1995 | Gevins | 128/731 |
| 5,465,321 A | 11/1995 | Smyth | 395/22 |
| 5,470,081 A | 11/1995 | Sato et al. | 273/438 |
| 5,474,082 A | 12/1995 | Junker | 128/732 |
| 5,485,551 A | 1/1996 | Ejima et al. | 395/61 |
| 5,515,335 A | 5/1996 | Swan | 367/47 |
| 5,515,477 A | 5/1996 | Sutherland | 395/27 |
| 5,524,176 A | 6/1996 | Narita et al. | 395/22 |
| 5,571,057 A | 11/1996 | Ayers | 463/36 |
| 5,579,439 A | 11/1996 | Khan | 395/11 |
| 5,583,771 A | 12/1996 | Lynch et al. | 364/424.045 |
| 5,585,646 A | 12/1996 | Kossovsky et al. | 257/40 |
| 5,617,513 A | 4/1997 | Schnitta | 395/50 |
| 5,651,100 A | 7/1997 | Hayashi et al. | 395/61 |
| 5,671,333 A | 9/1997 | Catlett et al. | 395/20 |
| 5,687,286 A | 11/1997 | Bar-Yam | 395/2.41 |
| 5,819,242 A | 10/1998 | Matsuoka et al. | 706/2 |
| 6,001,065 A | 12/1999 | DeVito | 600/544 |
| 6,012,017 A | 1/2000 | Van Bremmel et al. | 702/14 |
| 6,035,057 A | 3/2000 | Hoffman | 382/159 |
| 6,131,071 A * | 10/2000 | Partyka et al. | 702/16 |
| 6,546,378 B1 | 4/2003 | Cook | 706/12 |
| 2002/0059159 A1 | 5/2002 | Cook | |

OTHER PUBLICATIONS

Neura Ware Brochure, NeuralWorks Professional 11/PLUSv5.0, 2 pages.

J.J. Rajan and P.J.W. Rayner, "Unsupervised Time Series Classification," Signal Processing, vol. 46(1), pp. 57–74, May 4, 1995.

Reflection Seismic Date and Geopressure Formations, http://www.Ideo.columbia.edu/GBRN/he/paper/geopressure/seis_geop.html, 4 pages, Jul. 14, 2003.

Steffensen, Scott C. et al., *A novel Electroencephalographic Analysis Method Discriminates Alcohol Effects From Those of Other Sedative/Hypnotics*, Journal of Neuroscience Methods, Apr. 15, 2002, pp. 145–156, vol. 115, Issue 2.

* cited by examiner

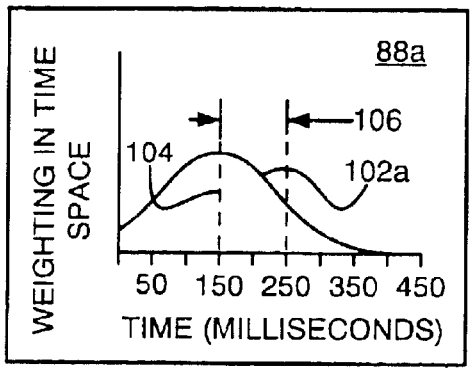
FIG. 7
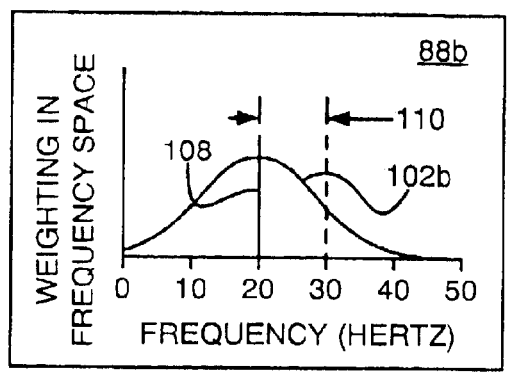
FIG. 8
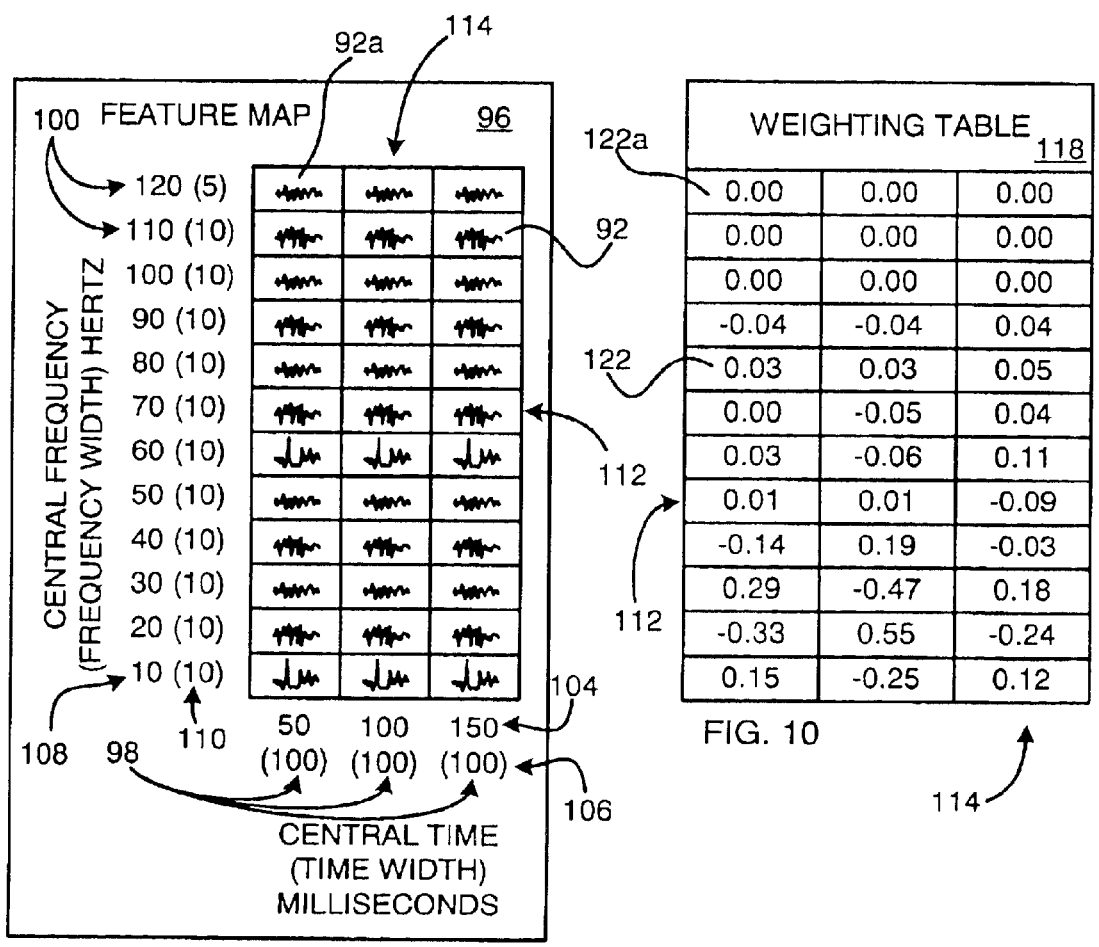
FIG. 9
FIG. 10

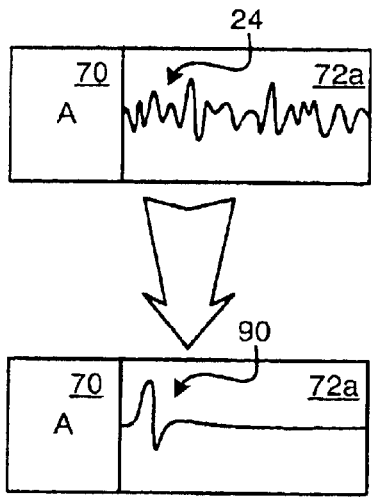
FIG. 11
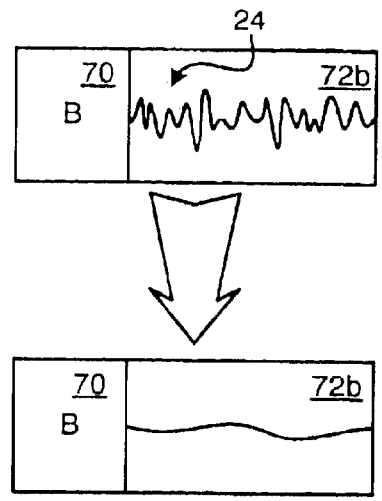
FIG. 12
| SEPARATION KEY | | | 80 |
|---|---|---|---|
| 120 (5) | 0.00 | 0.00 | 0.00 |
| 110 (10) | 0.00 | 0.00 | 0.00 |
| 100 (10) | 0.00 | 0.00 | 0.00 |
| 90 (10) | -0.04 | -0.04 | 0.04 |
| 80 (10) | 0.03 | 0.03 | 0.05 |
| 70 (10) | 0.00 | -0.05 | 0.04 |
| 60 (10) | 0.03 | -0.06 | 0.11 |
| 50 (10) | 0.01 | 0.01 | -0.09 |
| 40 (10) | -0.14 | 0.19 | -0.03 |
| 30 (10) | 0.29 | -0.47 | 0.18 |
| 20 (10) | -0.33 | 0.55 | -0.24 |
| 10 (10) | 0.15 | -0.25 | 0.12 |
| | 50 (100) | 100 (100) | 150 (100) |
CENTRAL FREQUENCY (FREQUENCY WIDTH) HERTZ
CENTRAL TIME (TIME WIDTH) MILLISECONDS
| OPTIMAL THRESHOLD VALUE | 138 |
|---|---|
| SUPERPOSITION PROCEDURE | 128 |
| AGGREGATION PROCEDURE | 130 |
FIG. 13

RELIABILITY MATRICES

|   | A | A |
|---|---|---|
| A | 49% | 51% |
| A | 48% | 52% |

→ $\underline{AA + AA}\over 2$ = $\underline{.49 + .52}\over 2$

156a ↙

|   | A | B |
|---|---|---|
| A | 88% | 12% |
| B | 10% | 90% |

→ $\underline{AA + BB}\over 2$ = $\underline{.88 + .90}\over 2$

156b ↙

|   | A | C |
|---|---|---|
| A | 75% | 25% |
| C | 20% | 80% |

→ $\underline{AA + CC}\over 2$ = $\underline{.75 + .80}\over 2$

156c ↙

194a → 196 ↶ 194a → 198 ↶

194b → 196 ↶ 194b → 198 ↶

194c → 196 ↶ 194c → 198 ↶

DISCRIMINATION MATRIX 162

|   | A | B | C |   | N |
|---|---|---|---|---|---|
| A | 49% | 89% | 78% | ... | 94% |
| B | 89% | 52% | 92% | ... | 87% |
| C | 78% | 92% | 50% | ... | 91% |
|   | ⋮ | ⋮ | ⋮ |   | ⋮ |
| N | 94% | 87% | 91% | ... | 51% |

194, 200

156n

|   | A | N |
|---|---|---|
| A | 92% | 8% |
| N | 5% | 95% |

→ $\underline{AA + NN}\over 2$ = $\underline{.92 + .95}\over 2$

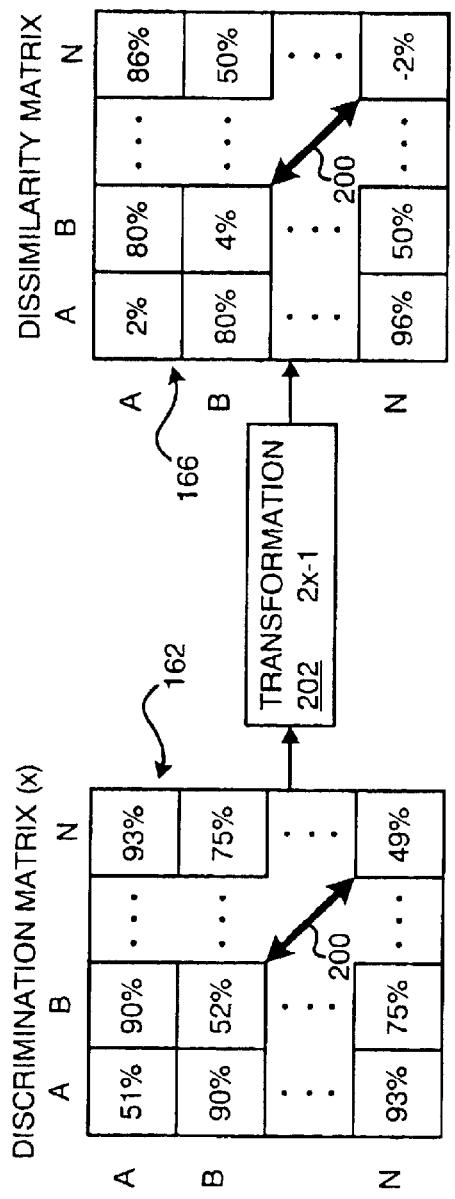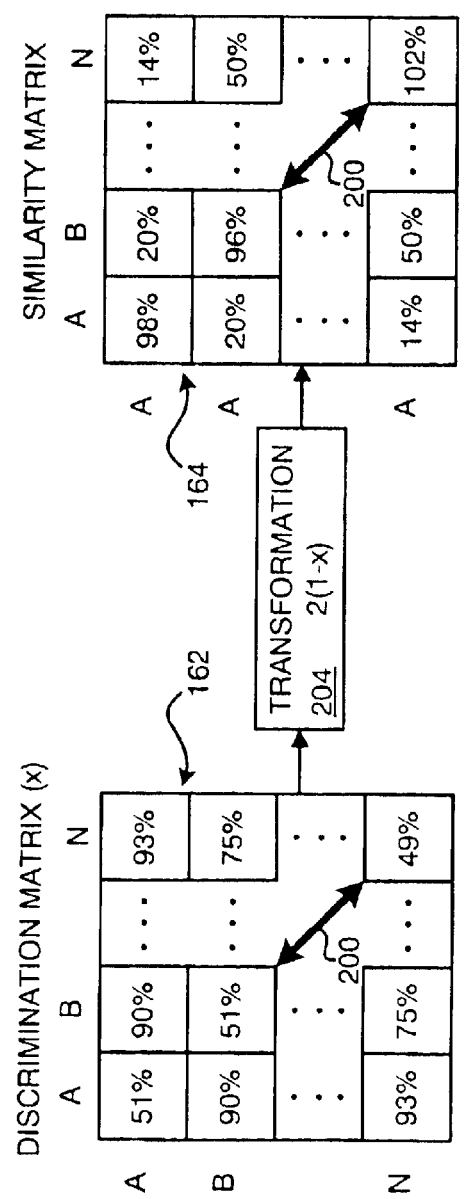

FIG. 31
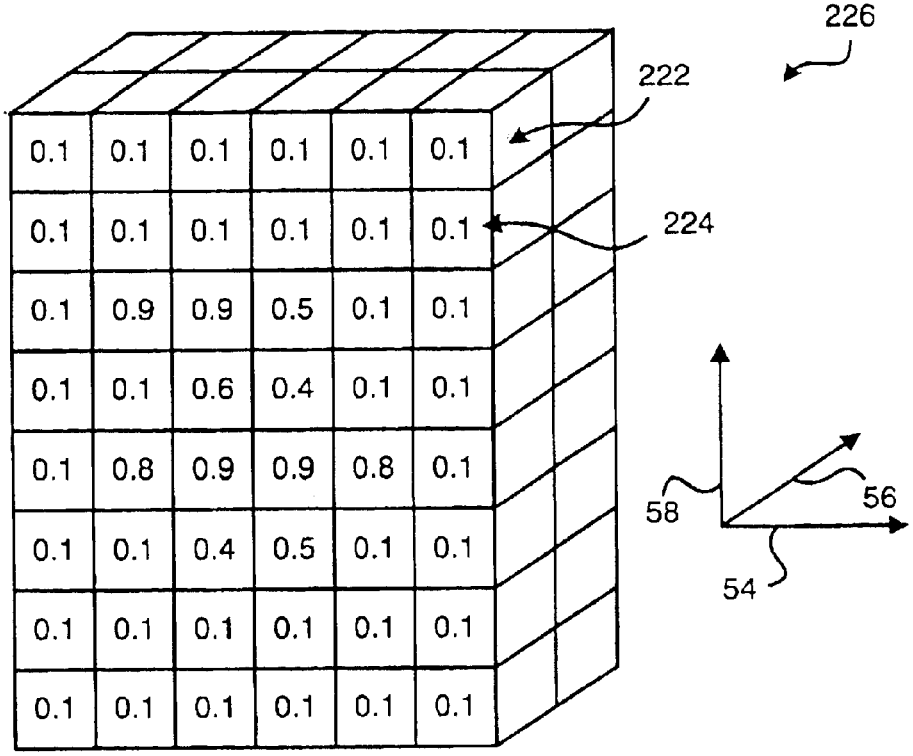
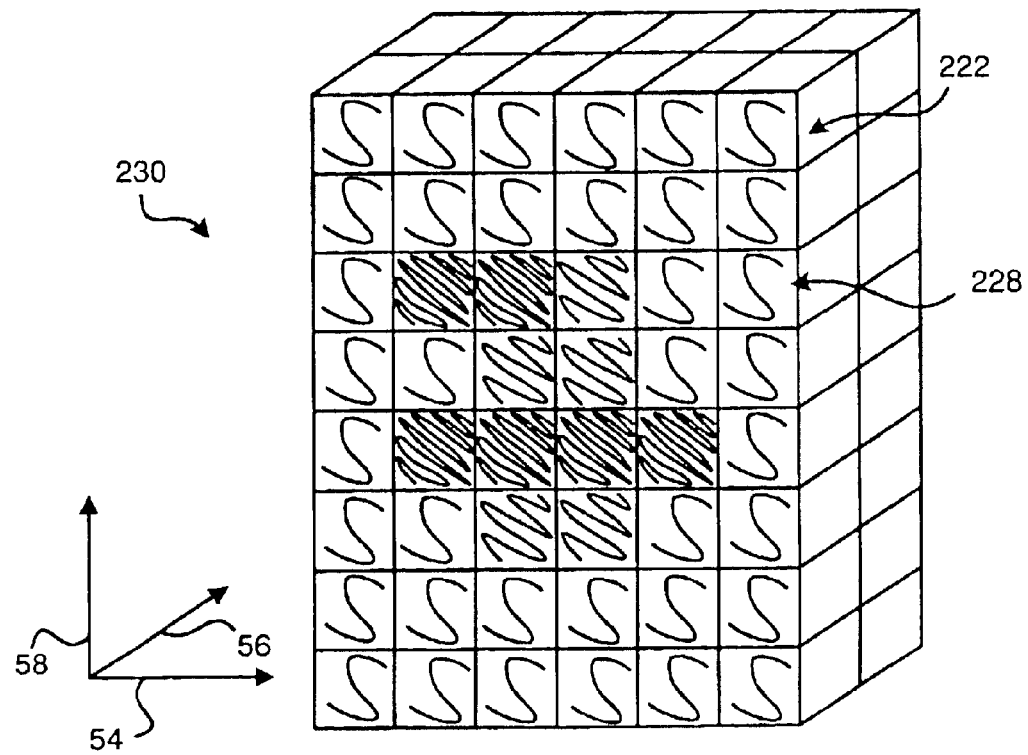
FIG. 32

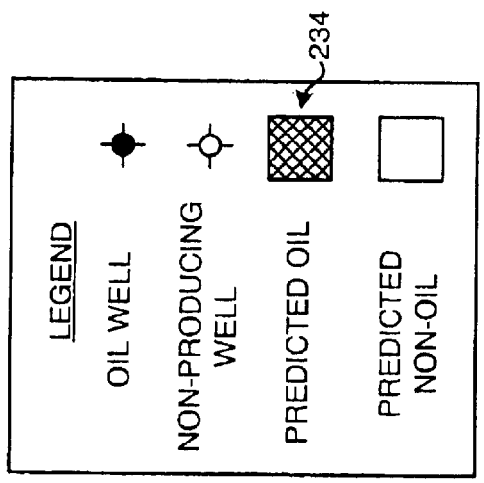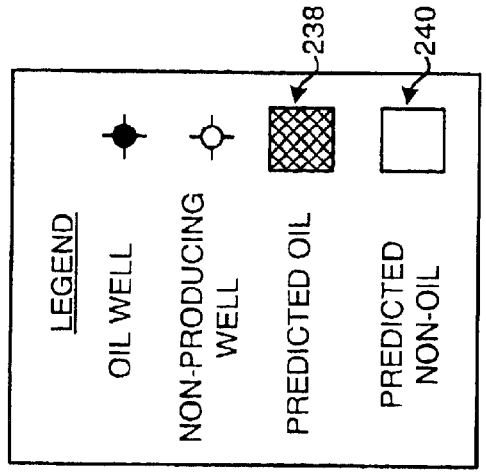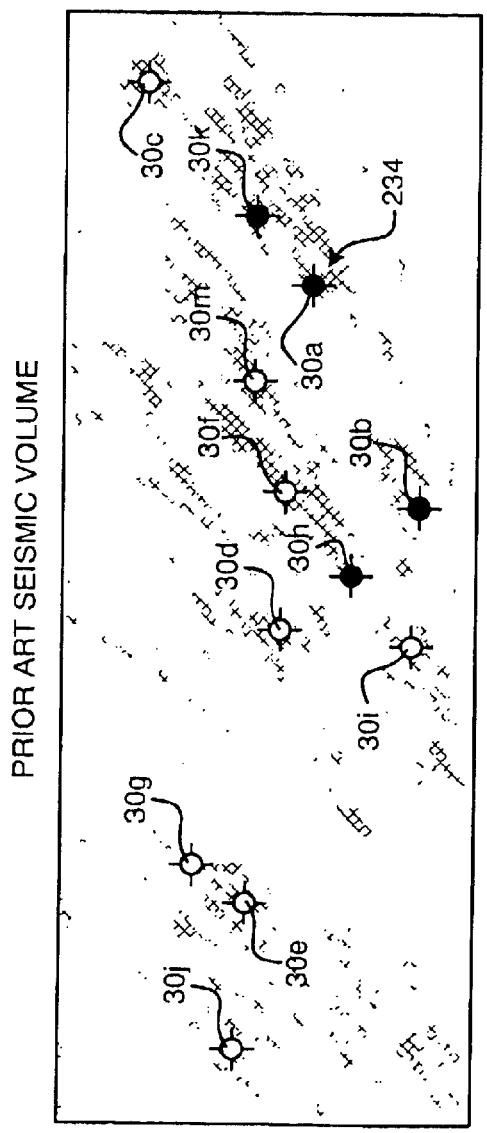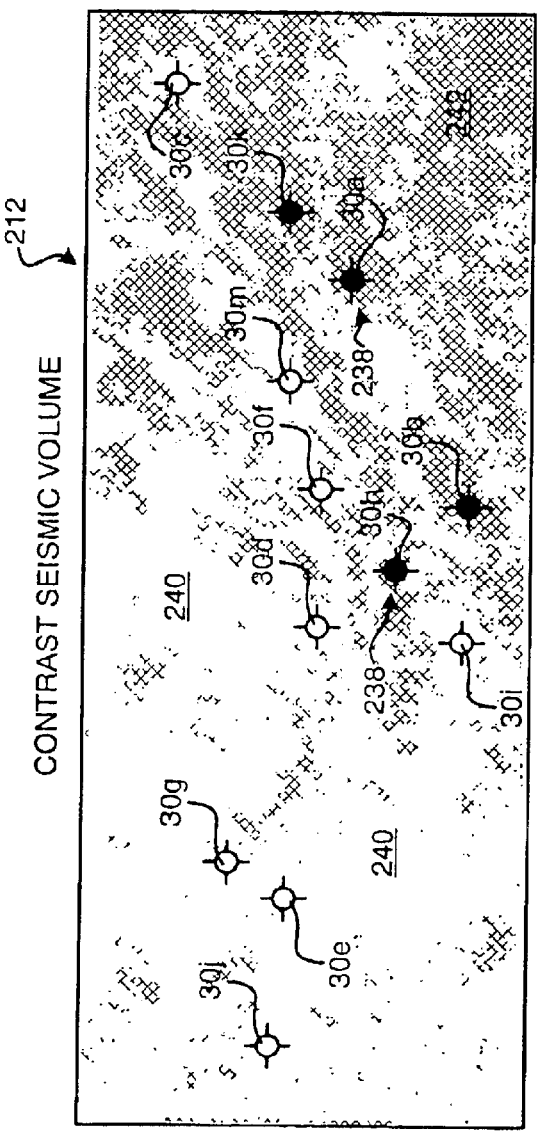
FIG. 37
FIG. 38

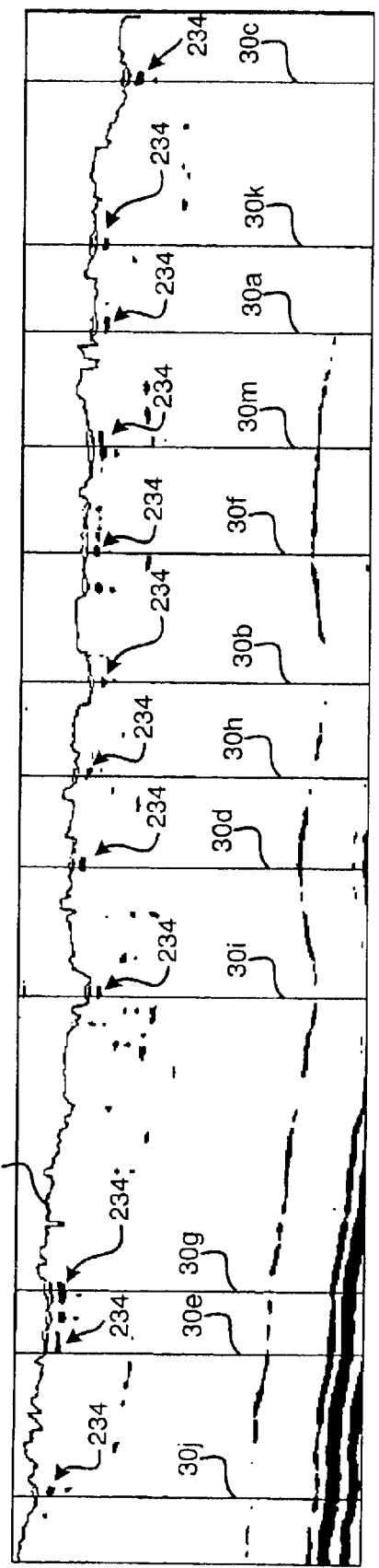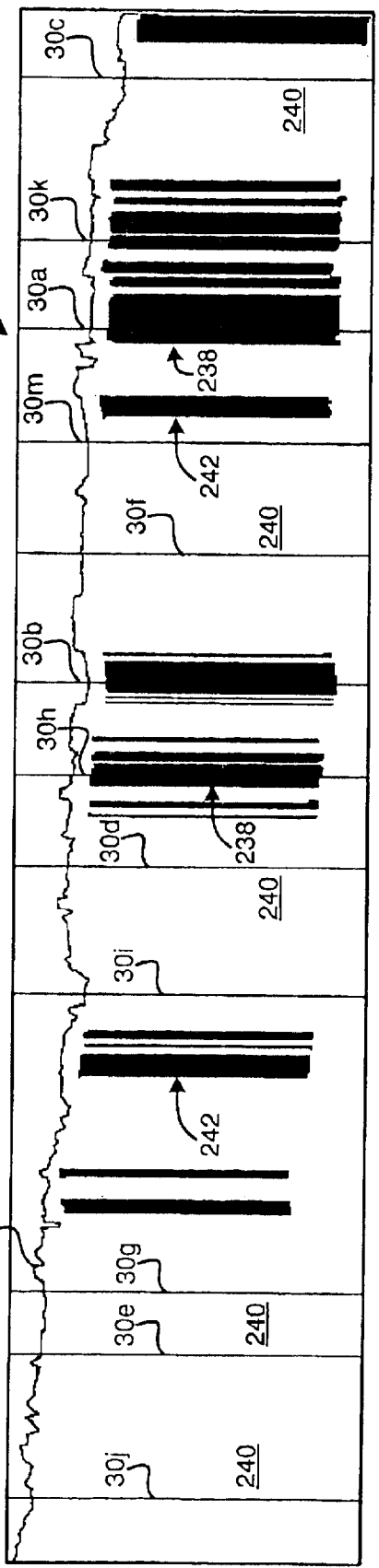

|  | WELL | STATE | TIME | TRACES | USE |
|---|---|---|---|---|---|
| 30a → | 1 | OIL | 0.976 - 1.176 | 169 | CLASSIFY |
| 30b → | 2 | OIL | 0.964 - 1.164 | 167 | LEARN |
| 30c → | 3 | DRY | 0.990 - 1.190 | 158 | LEARN |
| 30d → | 4 | DRY | 0.944 - 1.144 | 177 | CLASSIFY |
| 30e → | 5 | WET | 0.926 - 1.126 | 154 | LEARN |
| 30f → | 6 | WET | 0.960 - 1.160 | 171 | CLASSIFY |
| 30g → | 7 | UNKNOWN | 0.924 - 1.124 | 159 | CLASSIFY |
| 30h → | 8 | UNKNOWN | 0.950 - 1.150 | 163 | CLASSIFY |
| 30i → | 9 | UNKNOWN | 0.958 - 1.158 | 165 | CLASSIFY |
| 30j → | 10 | UNKNOWN | 0.920 - 1.120 | 163 | CLASSIFY |
| 30k → | 11 | UNKNOWN | 0.972 - 1.172 | 155 | CLASSIFY |
| 30m → | 12 | UNKNOWN | 0.966 - 1.166 | 170 | CLASSIFY |

| WELL | STATE | TIME | TRACES | USE |
|---|---|---|---|---|
| 1 | GAS | 0.75 - 0.95 | 481 | LEARN |
| 2 | WET | 0.75 - 0.95 | 606 | LEARN |
| 3 | TEST | 0.75 - 0.95 | 441 | CLASSIFY |
| 4 | TEST | 0.75 - 0.95 | 431 | CLASSIFY |
| 5 | TEST | 0.75 - 0.95 | 483 | CLASSIFY |
FIG. 44
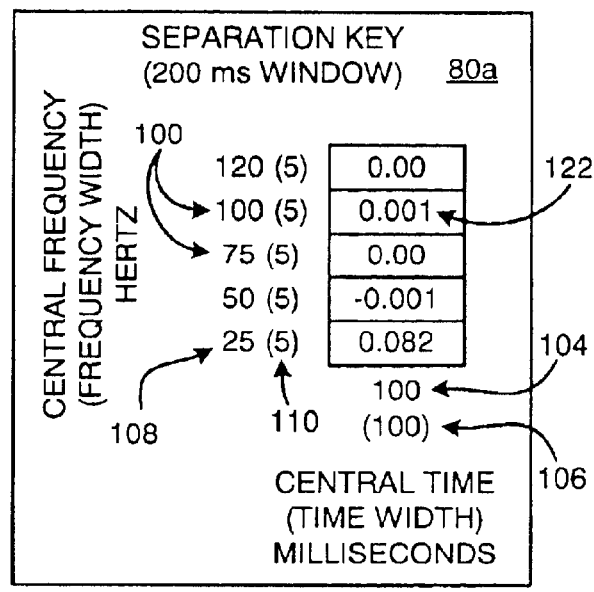
FIG. 45
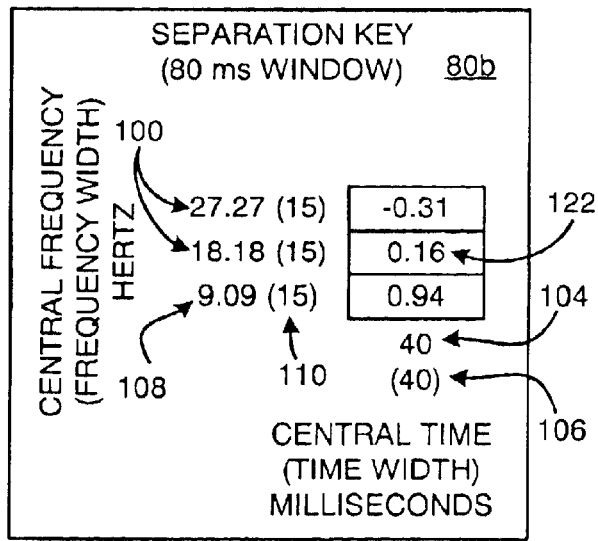
FIG. 46

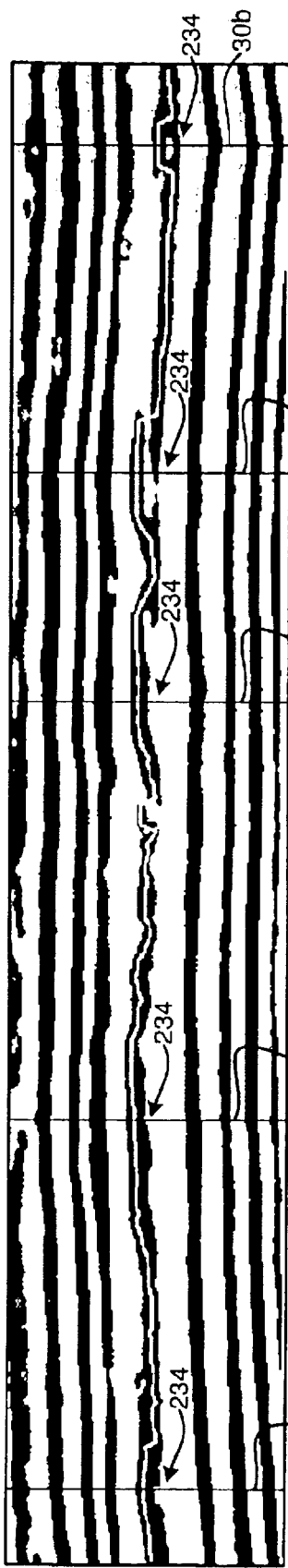
FIG. 47 PRIOR ART SEISMIC VOLUME
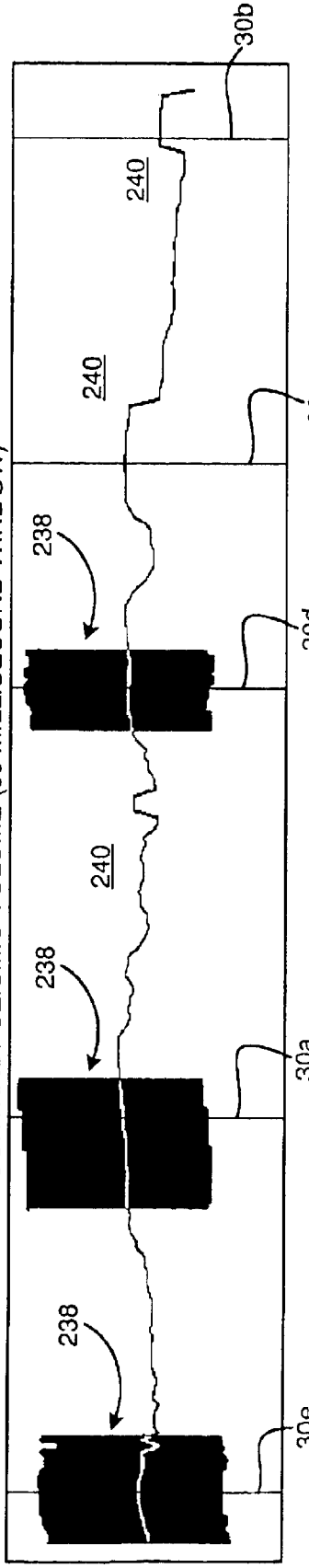
FIG. 48 CONTRAST SEISMIC VOLUME (80 MILLISECOND WINDOW)
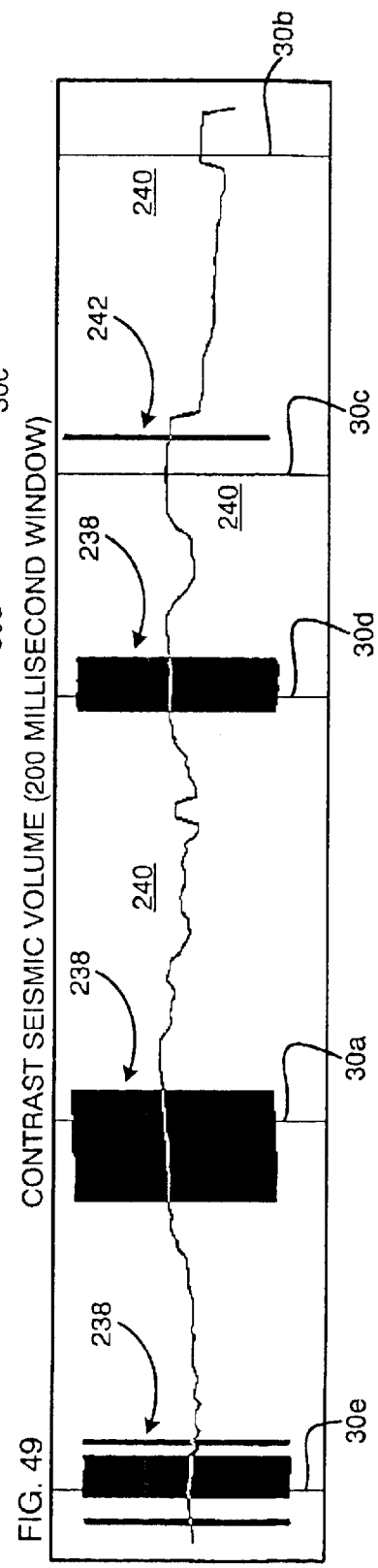
FIG. 49 CONTRAST SEISMIC VOLUME (200 MILLISECOND WINDOW)

PETROLEUM EXPLORATION AND PREDICTION APPARATUS AND METHOD

RELATED APPLICATIONS

This application claims the benefit of U.S. Provisional Application Ser. No. 60/416,342, filed Oct. 4, 2002, and entitled SEISMIC EVENT CONTRAST STACKING AND OTHER USES OF EVENT RESOLUTION IMAGING WITHIN THE OIL AND GAS INDUSTRY. Moreover, this application is a continuation-in-part of U.S. patent application Ser. No. 10/364,785, filed Feb. 11, 2003, now U.S. Pat. No. 6,745,156 and entitled SIGNAL INTERPRETATION ENGINE.

BACKGROUND

1. The Field of the Invention

This invention relates to signal processing and, more particularly, to novel systems and methods for pattern recognition and data interpretation relative to monitoring and categorizing patterns for predictably detecting and quantifying hydrocarbon deposits.

2. The Background Art

Seismic waves have been used to generate models of the earth's composition. In more recent times, seismic waves have been employed in an effort to located resources such as oil and gas deposits within the earth's surface formations. Well log data has also been applied to predicting resources within the earth. However, because of the low signal-to-noise ration (SNR) or high noise-to-signal ratio and complexity of seismic waves and well log data, generating accurate models of resource deposits has been difficult.

To facilitate the extraction of useful information, various types of signal processing strategies have been applied to seismic waves and well log data. Analysis strategies used by those skilled in the art have included spectral analysis, seismic trace stacking, various transforms, time-frequency distributions, spatial filtering methods, neural networks, fuzzy logic systems, and integrated neurofuzzy systems. As appreciated, each of these analysis techniques, however, typically relies on human inspection of the generated waveforms. Visual inspection may miss vital content that is implicit or hidden (e.g. time domain information).

Stacking of multiple seismic traces from pre-stack gathers generally employs summing or averaging signals acquired over many angles of incidence and many offsets. The end goal of stacking is to reduce noise and amplify certain, useful, seismic, waveforms. However, it further obscures other data. While useful for certain applications, averaging and stacking techniques have several significant drawbacks. Large quantities of information, just as valuable but less understood, are lost in the averaging or stacking. Only selected types of signals are able to survive massive averaging or summation over multiple offsets. Moreover, the averaging process only provides a comparison between groups of offsets or groups of angles rather than between the individual offsets or angles.

Alternative analysis approaches including Fourier Transforms; Hilbert Transforms; Wavelet Transforms; Short-Time Fourier Transforms; Wigner Functions; Generalized Time-Frequency Distributions; Parameter vs. Offset (PVO); and Amplitude vs. Offset (AVO) have been applied to seismic waves and well log data. While valuable for certain applications, these approaches typically require averaging over small groups of angles or small groups of offsets. Moreover, these approaches have not been fully integrated with computerized condition discrimination. Like spectral analysis techniques, these approaches rely on visual inspection of the generated waveforms, greatly increasing the possibility of error.

Spatial filtering methods, including: Principal Component Analysis; Singular Value Decomposition; and Eigenvalue Analysis have been applied to seismic waves and well log data. Such filtering methods tend to ignore frequency and temporal information. Additionally, these filtering techniques are usually applied only to seismic traces that have been averaged (post-stack seismic traces), otherwise the noise level is prohibitive.

Additional analysis techniques and methodology have been developed by those skilled in the art, to take advantage of recent increases in computer processing power. Neural networks have been developed to discover discriminate information. The traditional neural network approaches, however, generally take a long time to program and learn, are difficult to train, and tend to focus on local minima to the detriment of other more global and important areas. Moreover, most of these analysis techniques are limited by a lack of integration with time, frequency, and spatial analysis techniques.

Due to their inherent narrow ranges of applicability, prior methods of analysis have provided a fragmentary approach to seismic waves and well log data analysis. What is needed is an integrated waveform analysis method capable of extracting useful information from highly complex and irregular waveforms such as raw seismic data, pre-stack seismic gathers, post-stack seismic traces, and the variety of signal types comprising well log data sets.

BRIEF SUMMARY OF THE INVENTION

In accordance with the invention as embodied and broadly described herein, apparatus and methods in accordance with the present invention may include an event contrast stacker arranged to process seismic traces, well log data, and the like to produce reliable and accurate information about a geological formation. Particularly, characteristic signals relating to a geological formation may be gathered, amplified, processed, and recorded. Such signals may include seismic traces (raw traces, pre-stack gathers, post-stack gathers, and the like), well log data, and any other waveform or measured value believed to contain information as to the content, state, or composition of the geological formation.

The strategy of an event contrast stacker in accordance with the present invention is to apply several methods of analysis to each epoch (time period of interest) to find and exhibit consistent differences between epochs relating to different states and similarities between epochs related to similar states. An event contrast stacker may include a signal pre-processor, a learning system, a classification system, and an output generator.

A signal pre-processor may provide any filtering, amplification, and the like that may prepare the signal for further processing. Additionally, the signal pre-processor may divide the signal into time segments or epochs. Each epoch may be labeled according to the state, if known, of the geological formation from which the data pertaining to an epoch was collected.

A collection of data from epochs, where the physical system represented thereby is of a known state may be passed to a learning system. The learning system may use several waveform analysis techniques including, by way of example and not limitation, time-frequency expansion, feature coherence analysis, principal component analysis, and separation analysis. For convenience we may refer to any set of data recorded over an epoch of time and relating to the same sensed system as an "epoch," even though an epoch is literally just the application time segment. Each epoch may be expanded by feature operators (mathematical manipulations applying waveform analysis techniques) to generate feature segments in an extended phase space representing spatial, time, frequency, phase, and interchannel relationships. The various feature segments corresponding to an epoch may be weighted in an effort to locate the feature segments containing information corresponding exclusively to the state of the epoch. Weightings or weights may be though of as respective coefficients for each mathematical function contributing to composite or sum of contributing functions. Thus a weight is a proportion of contribution of a function or value.

Once weighted, the feature segments corresponding to an epoch may be summed or superimposed. If successful, the superposition provides a resulting waveform containing a non-random feature or pattern uniquely corresponding to the state of the epoch. If unsuccessful, the operation provides no distinction and the learning system may begin another iteration and apply a different combination of feature operators, feature weights, or both feature operators and feature weights. The learning system may continue processing until the superimposed feature segments of an epoch result in a characteristic feature corresponding exclusively to the state of the epoch. Once the effective feature operators, feature weights, and the like have been determined, they may be incorporated into a separation key. A separation key provides feature operators and weights, along with a resulting waveshape or other characteristic that will reliably distinguish two opposing states.

In one embodiment of a system in accordance with the present invention, a classification system may use the separation key and apply the feature operators and weights (previously determined to be optimal) to a selected group of epochs referred to as classification epochs. Classification epochs may have known states or unknown states. True epoch state labels may be bound to analyzed epochs to enable a comparison with epoch classifications generated by the classification system. That is, the actual or true state associated with a particular epoch may provide a key to determine if that epoch has been correctly classified. Accordingly, this may provide a method of testing or validating the accuracy of an event contrast stacker. High classification accuracy of non-training epochs (separate and distinct from the learning epochs used in the creation of the separation key), indicates a valid, derived, separation key capable of repeatedly separating signals according to the state of the geological formation from which the signals were collected.

The classification system may forward certain data to an output generator to compile a statistical summary of the results. Additional outputs may include calculations of sensitivity, specificity and overall accuracy.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of apparatus and methods in accordance with the invention and are, therefore, not to be considered limiting of its scope, the invention will be described with additional specificity and detail through use of the accompanying drawings in which:

FIG. 7 is a graph of a feature operator comprising a weighting in a time space (domain);

FIG. 8 is a graph of a feature operator comprising a weighting in a frequency space (domain);

FIG. 9 is a table illustrating a feature map in accordance with the present invention wherein the signal epoch has been expanded into three time segments and twelve frequency segments to generate a total of thirty-six feature segments;

FIG. 10 is a table illustrating an embodiment of a weighting table have weights to be applied to the feature segments of FIG. 9 in accordance with the present invention;

FIG. 11 is a schematic block diagram illustrating an example epoch corresponding to a state A before and after processing by an event contrast stacker in accordance with the present invention;

FIG. 12 is a schematic block diagram illustrating an example epoch corresponding to a state B before and after processing by an event contrast stacker in accordance with the present invention;

FIG. 13 is a table illustrating an embodiment of a separation key generated by a learning system in accordance with the present invention;

FIG. 22 is a schematic block diagram illustrating the formation of a discrimination matrix by an output generator in accordance with the present invention;

FIG. 23 is a schematic block diagram illustrating the formation of a dissimilarity matrix by an output generator in accordance with the present invention;

FIG. 24 is a schematic block diagram illustrating the formation of a similarity matrix by an output generator in accordance with the present invention;

FIG. 31 is a schematic diagram of a number plot corresponding to the seismic contrast volume of FIG. 27 in accordance with the present invention;

FIG. 32 is a schematic diagram of a color plot corresponding to the seismic contrast volume of FIG. 27 in accordance with the present invention;

FIG. 37 is a two-dimensional, horizontal image derived, using prior art methods, from actual seismic data collected from an oil field;

FIG. 38 is a two-dimensional, horizontal image derived from data generated by an event contrast stacker in accordance with the present invention from seismic data collected from the oil field;

FIG. 39 is a two-dimensional, vertical image derived, using prior art methods, from actual seismic data from the oil field;

FIG. 40 is a two-dimensional, vertical image derived from data generated by an event contrast stacker in accordance with the present invention from seismic data collected from the oil field;

FIG. 44 is a table illustrating the status, time window examined, and number of traces processed in accordance with the present invention for each of the various wells drilled in a gas field;

FIG. 45 is a table illustrating a portion of one embodiment of a separation key found by an event contrast stacker, in accordance with the present invention, to be effective over an 80 millisecond window on seismic data collected from the gas field;

FIG. 46 is a table illustrating a portion of an alternative embodiment of a separation key found by an event contrast stacker in accordance with the present invention to be effective over a 200 millisecond window on seismic data collected from the gas field;

FIG. 47 is a two-dimensional, vertical image derived, using prior art methods, from actual seismic data collected from the gas field;

FIG. 48 is a two-dimensional, vertical image derived from data generated by an event contrast stacker in accordance with the present invention over an 80 millisecond window of seismic data collected from the gas field;

FIG. 49 is a two-dimensional, vertical image derived from data generated by an event contrast stacker in accordance with the present invention over a 200 millisecond window of seismic data collected from the gas field;

DETAILED DESCRIPTION

It will be readily understood that the components of the present invention, as generally described and illustrated in the Figures herein, could be arranged and designed in a wide variety of different configurations. Thus, the following more detailed description of the embodiments of the system and methods in accordance with the present invention, as represented by FIGS. 1 through 51, is not intended to limit the scope of the invention, as claimed, but is merely representative of the presently preferred embodiments of the invention.

Certain embodiments of apparatus and methods in accordance with the present invention incorporate the hardware and software of the signal interpretation engine disclosed in U.S. Pat. No. 6,546,378, filed Apr. 24, 1997, and entitled SIGNAL INTERPRETATION ENGINE, incorporated herein by reference. The present application does not attempt to describe every detail of the signal interpretation engine. To this end, the details of the signal interpretation engine are contained in the patent specification directed thereto. Whereas, only a general description of selected modules and procedures is presented herewith.

Figure 1:
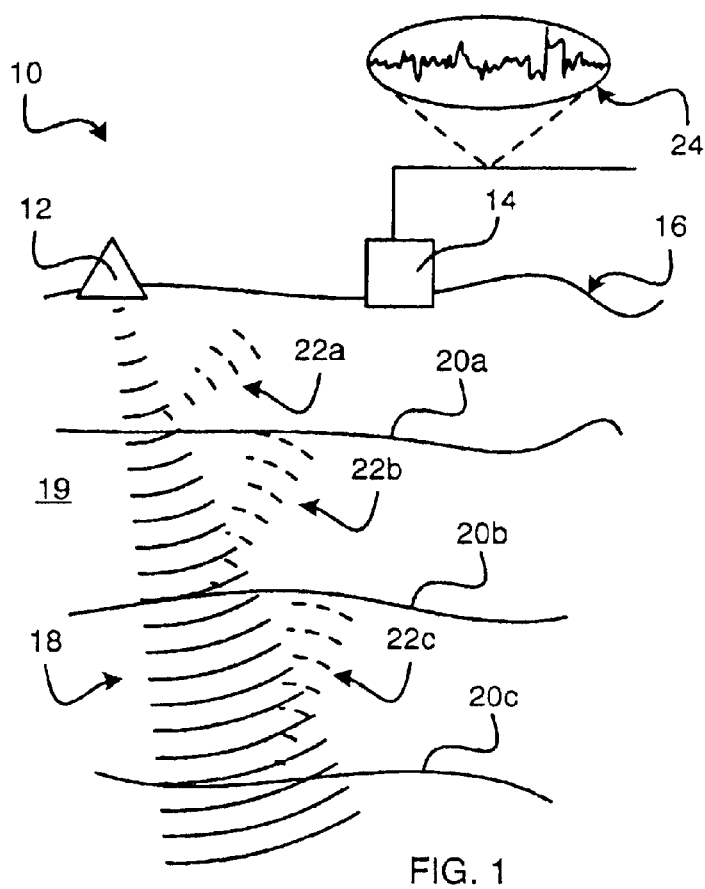
FIG. 1 is a schematic diagram of a geological formation having primary seismic waves propagated therethrough and reflected seismic waves recorded therefrom.

Referring to FIG. 1, in general, a seismic study 10 may be conducted by positioning at least one source 12 and at least one receiver 14 on, above, or within the earth's surface 16. A source 12 may generate a primary seismic wave 18 in a selected geological area 19 or geological formation 19. As a primary wave 18 travels though the geological formation 19, it may encounter reflectors 20. Reflectors 20 may be changes in the earth's make-up, striations, strata, differentials in density, differentials in stiffness, differentials in elasticity, differentials in porosity, changes in phase, and the like. Various reflectors 20a, 20b, 20c may reflect the primary wave 18 creating corresponding reflected seismic waves 22a, 22b, 22c. The reflected waves 22 may be recorded, in the order of their arrival, by a receiver 14. Reflected waves 22 gathered by a receiver 14 may be used to interpret the composition, fluid content, extent, geometry, and the like of geological formations 19 far below the earth's surface 16.

In general, sources 12 may be selected from any devices for generating a seismic wave 20. Suitable sources 12 may include air guns, explosive charges, vibrators, vibroseis trucks, and the like. A receiver 14 may be any device that detects seismic energy in the form of ground motion (or a pressure wave in fluid) and transforms it to an electrical impulse 24 or signal 24. Generally, receivers 14 are referred to as geophones, for use on land, and hydrophones, for use on water. The electrical impulse 24 recorded by a receiver 14 may be referred to as a seismic trace 24. A trace 24 may, therefore, be defined as a recording of the response of the earth 19 to seismic energy passing from a source 12, through subsurface layers (reflectors 20), and back to a receiver 14.

The seismic waves 18, 22 produced by a source 12 and recorded by a receiver 14 are generally in the frequency range of approximately 1 to 120 Hz. Seismic waves 18, 22 may be divided into two main categories, namely, pressure waves and shear waves. Pressure waves are elastic body waves or sound waves in which particles oscillate in the direction the wave propagates. Shear waves are elastic body waves in which particles oscillate perpendicular to the direction in which the wave propagates. Shear waves may be generated when pressure waves impinge on an interface at non-normal incidence. Shear waves can likewise be converted to pressure waves.

Figure 2:
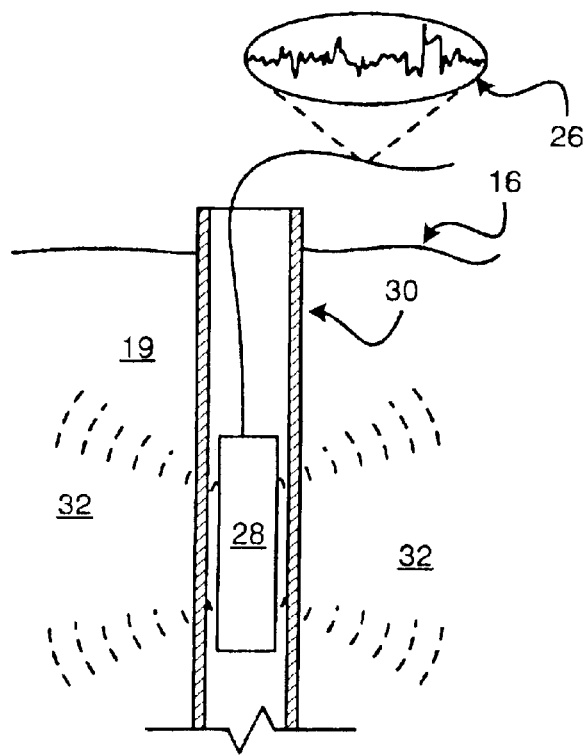
FIG. 2 is a schematic diagram of a well undergoing well log data collection.

Referring to FIG. 2, in certain applications, well log data 26 may be used to provide additional information about selected geological formations 19 below the earth's surface 16. Well log data 26 may be collected by lowering an instrument array 28 into a well bore 30. The instrument array 28 may measure or record any characteristic of the well environment 32. For example, an instrument array 28 may emit various waves into the well environment 32 and record the response. Additionally, an instrument array 28 may measure temperature, pressure, conductivity, and the like of the well environment 32. Well log data 26 may be used to better understand geological formations 19 penetrated by wells 30.

Figure 3:
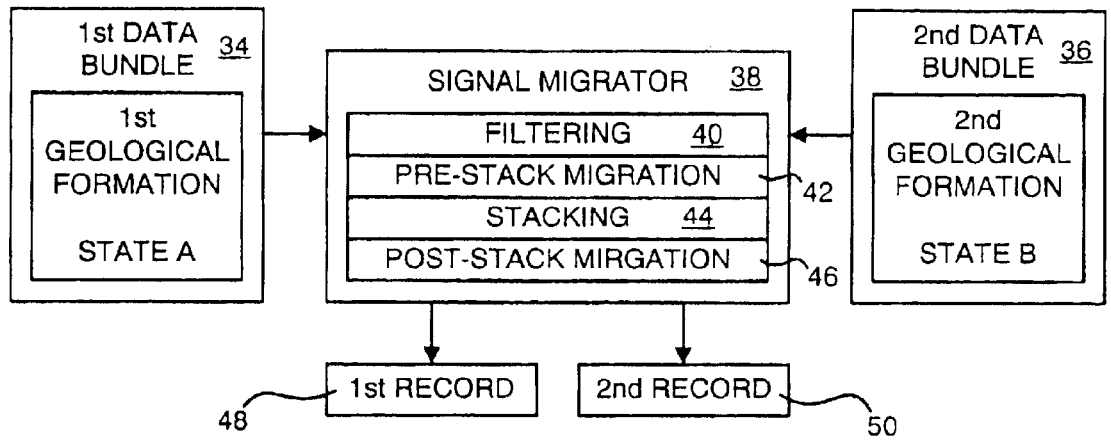
FIG. 3 is a schematic block diagram illustrating a signal migrator in accordance with the present invention.

Referring to FIG. 3, in certain embodiments of apparatus and methods in accordance with the present invention, a geologic study 10 may collect a first data bundle 34, corresponding to a first geological formation 19 having state A. In a similar manner, a geological study 10 may collect a second data bundle 36, corresponding to a second geological formation 19 having state B. The data bundles 34, 36 may contain seismic traces 24, well log data 26, some other measured signal, value, or the like, or any combination thereof.

Hereinafter, data processed in accordance with the present invention may be referred to generically as a signal 24. However, it should be recognized that a signal 24 may include seismic traces 24 (e.g. raw traces, pre-stack gathers, post-stack gathers, attribute volumes, and the like), well log data 26, and any other waveform or measured value containing information as to the content, state, or composition of a geological formation 19.

In embodiments utilizing seismic traces 24, the data bundles 34, 36 may be processed by a signal migrator 38. In general, a signal migrator 38 may process traces 24 by applying filtering 40, a pre-stack migration 42, stacking 44, a post-stack migration 46, or any combination thereof. After processing of signals 24 by the signal migrator 38, the signal migrator 24 may provide a first record 48 to store data corresponding to the first data bundle 34. A second record 50 may be generated to store data corresponding to the second data bundle 36.

A "migration" 42, 46 of a seismic trace 24 is a complex process to determine the location in three-dimensional space from which the trace 24 most likely originated. Migration 42, 46 often involves applying a predicted velocity profile for the geological area 19 being studied. That is, various materials transfer seismic waves 18, 22 at different velocities. By taking what is known about a particular geological formation 19, an estimate may be formulated for how long it would take a primary seismic wave 18 to travel down to a particular reflector 20, reflect, and travel as a reflected seismic wave 22 back to the surface 16. The longer the time for a reflected wave 22 to arrive at the surface 16, the deeper the reflector 20 and origin of the trace 24 is likely to be. This process may, however, be complicated by the ability of waves 18, 22 to reflect back and forth between reflectors 20 before arriving at the surface. Thus, the travel time of certain signals 24 may be artificially prolonged.

Using velocity profiles and various other techniques, geologists may provide an approximation of the location where a trace signal 24 was generated in three-dimensional space. This locating process may be important because it ties the information contained within a trace 24, or a portion of a trace 24, to a particular location.

Stacking 44 is often simply the averaging or summing of a signal 24 with other signals 24 collected by the same receiver 14 or by other receivers 14 in the same area. Stacking 44 is typically used in an attempt to amplify common characteristic of the signals 24. However, in certain applications, stacking 44 by averaging or summing may destroy or cancel useful information.

The first and second records 48, 50 may be generated at various stages during processing by a signal migrator 38. For example, the first and second records 48, 50 may be generated upon completion of the pre-stack migration 42, stacking 44, or the post-stack migration 46. Traces 24 processed only through a pre-stack migration 42 may be referred to as pre-stack gathers. Pre-stack gathers may be rich with hidden information. However, traces 24 processed through a post-stack migration 46 (generally referred to as post-stack gathers) may also contain sufficient informational content to be useful.

In general, data 34, 36 not in the form of a seismic trace 24 collected from the surface 16 need not be processed by a signal migrator 38. Migration 42, 46, which is essentially an attempt to locate the source of signals 24 that have traveled large distances, is not necessary when the source of the data is already known. For example, well log data 26 by definition is tied to the area surrounding a well 30, thus migration 42, 46 may not be needed. It should be recognized, however, that data 34, 36 in any form may be filtered, amplified, or otherwise processed as needed before the first 48 and second records 50 are generated.

Figure 4:
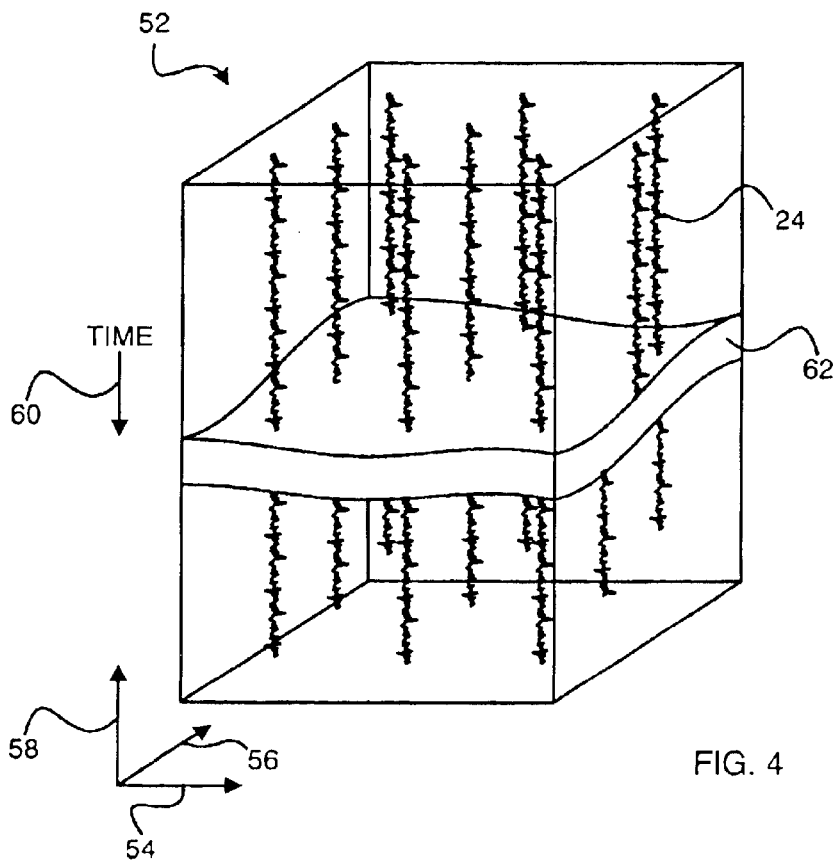
FIG. 4 is a perspective view of a three dimensional seismic volume comprising a collection of seismic traces.

Referring to FIG. 4, first and second data bundles 34, 36 in accordance with the present invention may represent any collection of information. In certain embodiments, a data bundle 34, 36 may comprise all, or any portion, of a three-dimensional seismic volume 52. A three-dimensional seismic volume 52 may be any mathematical space (domain), defined by an X-axis 54, Y-axis 56, and Z-axis 58, containing a selected number of signals 24 positioned therewithin. A three-dimensional seismic volume 52 may be aligned so increasing time 60 of the recorded signals 24 is aligned with the Z-axis 58. Thus, progress in the negative direction along the Z-axis 58 may indicate increasing time 60 as well as increasing depth into the earth 19.

As stated hereinabove, a data bundle 34, 36 may comprise all, or any portion, of a three-dimensional seismic volume 52. Thus, a data bundle 34, 36 may represent a single signal 24, a portion of a single signal 24, multiple signals 24, or portions of multiple signals 24. If portions of multiple signals representing a particular value of time (depth) are utilized, the collection may be referred to as a horizon 62. A data bundle 34, 36 comprising a horizon may be useful for extracting information about a particular "pay horizon" or other suspected hydrocarbon deposit.

Figure 5:
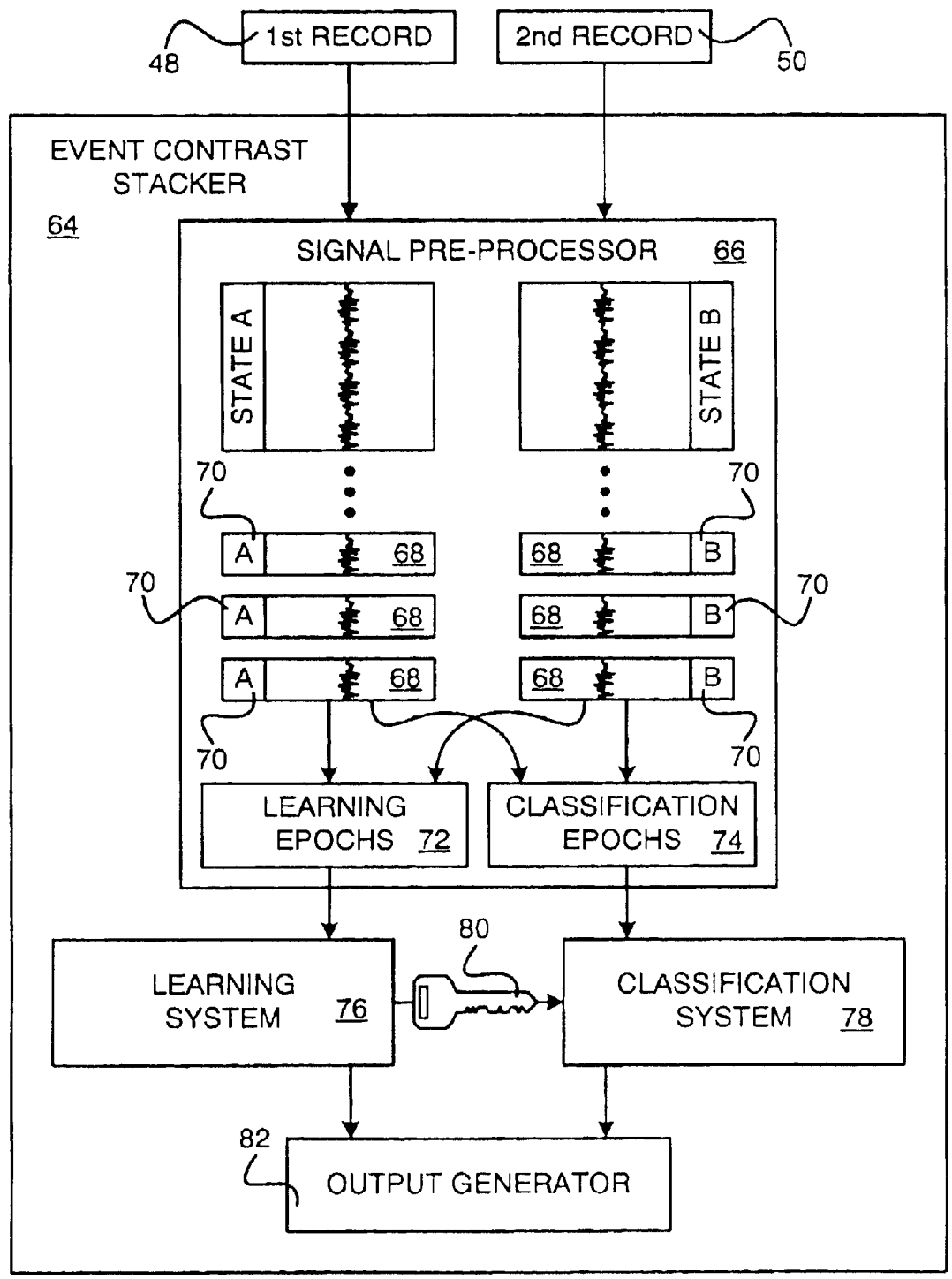
FIG. 5 is a schematic block diagram of an embodiment of an event contrast stacker in accordance with the present invention.
Figure 6:
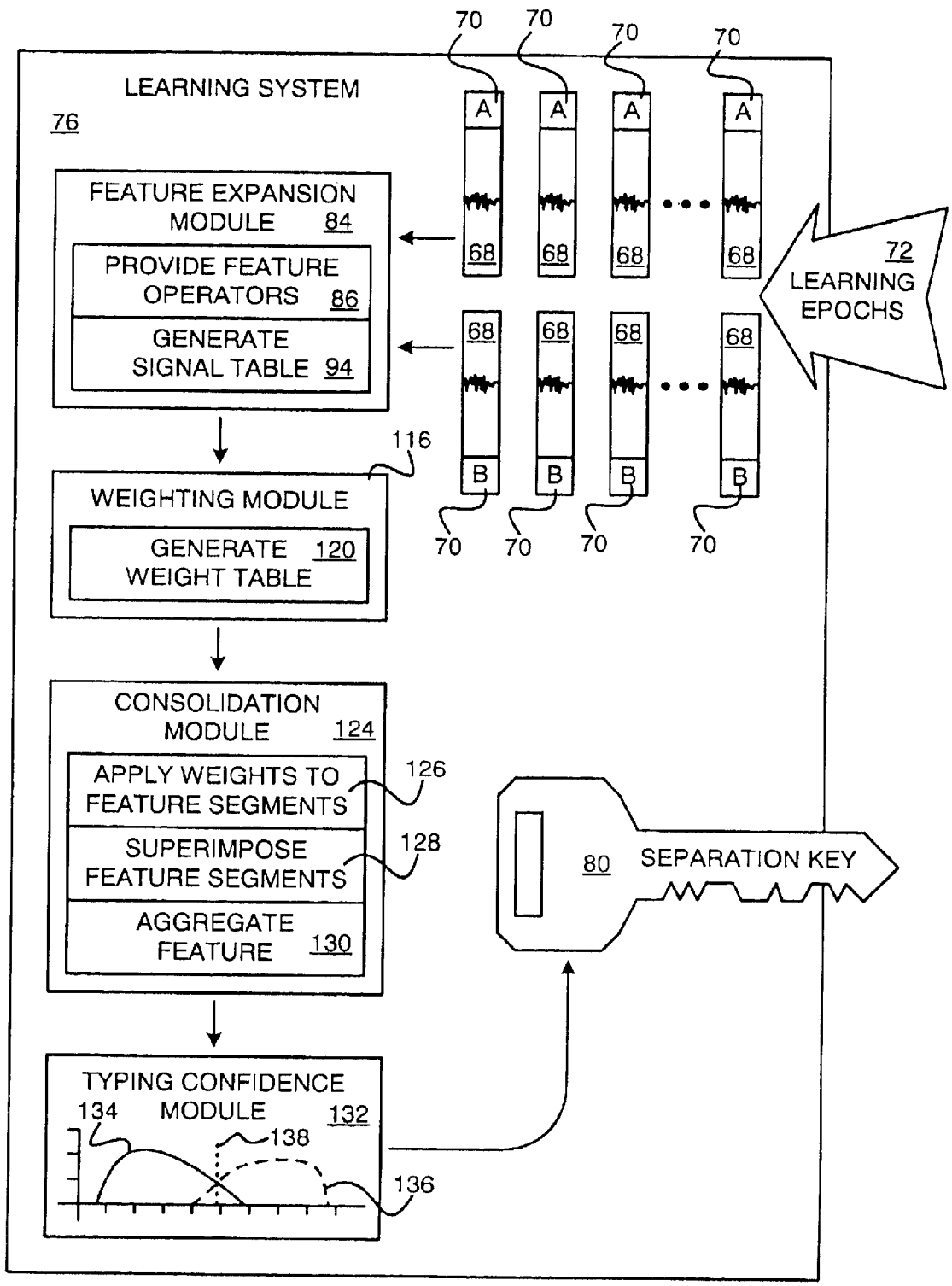
FIG. 6 is a schematic block diagram of an embodiment of a learning system from an event contrast stacker in accordance with the present invention.

Referring to FIG. 5, once processed as desired, the first and second records 48, 50 may be forwarded to a event contrast stacker 64. In certain embodiments, an event contrast stacker 64 in accordance with the present invention applies several methods of analysis to the data bundles 34, 36 to find consistent similarities within signals 24 related to similar states and differences between signals 24 relating to different states.

In certain embodiments, an event contrast stacker 64 may begin by passing the first and second records 48, 50 through a signal pre-processor 66. The signal pre-processor 66 may divide the records 48, 50 into epochs 68. An epoch 68 may be defined as a time segment of a signal 24. A label 70 may be applied to each epoch 68 to identify the state of the geological formation 19 from which the epoch 68 was collected. For example, epochs collected from a first geological formation 19 may have a label indicating that the epochs correspond to a state A. Similarly, epochs from a second geological formation 19 may have a label indicating that the epochs correspond to a state B, Not-A and distinct from A.

The state of a geological formation 19 may be any characteristic of the formation 19 whose presence or absence may be worth predicting, quantifying, or the like. In general, state A may be the presence of a characteristic, while state B is the absence of the characteristic. Thus, state B is typically the state Not-A. For example, state A may be the presence of a hydrocarbon deposit, while state B is the absence of a hydrocarbon deposit. State A may be oil production above an threshold value, while state B is oil production below a threshold value. Other suitable state pairs include: presence of sand, absence of sand; presence of shale, absence of shale; density above a threshold value, density below a threshold value; water content above a threshold value, water content below a threshold value; porosity above a threshold value, porosity below a threshold value; gas production above a threshold value, gas production below a threshold value; permeability above and below a threshold value; presence and absence of salt; presence and absence of absorbed noncondensible gases (fizz water); presence and absence of faults; or the like.

In selected embodiments, states A and B may be differentiated economically. For example, state A may be hydrocarbon production over $1000 per day, while state B may be hydrocarbon production below $50 per day. In another embodiment, state A may be an economically viable hydrocarbon well (production sufficient to cover operating costs), while state B is a non-economically viable hydrocarbon well (production insufficient to cover operating costs). In short, states A and B may be any two determinable conditions, qualities, characteristics, production rates, or the like of geological formations 19.

In certain embodiments, the labels 70 applied to the epochs 68 may also contain location information. For example, a label 70 may contain a coordinate (e.g. ordered triplet), or other designation, to identify the location of the epoch 68 in a three-dimensional or other seismic volume 52.

Once segmented and labeled, a selected number of the epochs 68, each known to represent a known state A or state B, may be designated as learning epochs 72. Similarly, a selected number of the epochs 68 unknown as to their representing state A or state B may be designated as classification epochs 74. The learning epochs 72 may be forwarded to a learning system 76 while the classification epochs 74 may be forwarded to a classification system 78.

In selected embodiments, the learning system 76 may operate on the learning epochs 72 until a suitable interpretation map 80 or separation key 80 is generated. A separation key 80 may be considered complete when, upon application thereof to the learning epochs 72, a non-random pattern corresponding to one of state A or state B is generated. After formulation, the separation key 80 may be transmitted to the classification system 78. In certain embodiments, the classification system 78 may provide a test to verify the utility of the newly generated separation key 80. Additionally, the classification system 78 may analyze and expand the classification epochs 74 in accordance with the information supplied by the separation key 80.

At any time during processing, selected information may be exported from the learning system 76, the classification system 78, or both the learning system 76 and the classifications system 78, to an output generator 82 for conversion into a useful and easily accessible format.

In selected embodiments, an event contrast stacker 62 may be incorporated into a single unit incorporating both hardware and software in accordance with the present invention. In such a configuration, a drive, network connection, or the like may be provided for receiving the first and second records 48, 50. In an alternative embodiment, an event contrast stacker 64 may simply be a personal computer having an appropriate hardware and software configuration sufficient to provide a desired level of data reception, recordation, amplification, and manipulation capabilities.

Those skilled in the art will readily recognize that various other modules or systems may be incorporated in connection with an event contrast stacker 64 in accordance with the present invention. It is intended, therefore, that the examples provided herein be viewed as exemplary of the principles of the present invention, and not as restrictive to particular structures, systems, modules, or methods for implementing those principles.

Referring to FIGS. 6–13, the learning system 76 may receive and process learning epochs 72 to compile an optimized formula (i.e. separation key 80) for segregating epochs 72 by state. Within a learning system 76, learning epochs 72 may first be processed in a feature expansion module 84. A feature expansion module 84 may provide 86 a collection of feature operators 88 comprising various mathematical manipulations. The collection of feature operators 88 may be stored within the feature expansion module 84 or input by a user. Additionally, a feature expansion module 84 may also be arranged to store a collection of feature operators 88 as well as receive feature operators 88 input by a user.

By processing each epoch 72 through a multitude of feature operators 88, unique characteristics 90 or features 90 corresponding to a particular state may be magnified to the point that they become easily discernable to a computerized criterion or to a discerning user. A feature 90 may be any non-random pattern corresponding exclusively to epochs 72 of a particular state, as opposed to "not that particular state." While certain feature operators 88, or combinations of feature operators 88, may be effective to produce repeatable features 90 in epochs 72 of a common state, other feature operators 88 may be ineffective. By processing the epochs 72 with a collection of feature operators 88, the most effective feature operators 88 or combination of feature operators 88 may be identified.

In selected embodiments, the feature expansion module 84 may process each epoch 72 individually. In other embodiments, the feature expansion module 84 may consolidate epochs 72 before processing. For example, when multiple input signals 24 are contained within an epoch 72, the feature expansion module 84 may superimpose any combination of the input signals 24 to create a composite signal. Selected signals 24 of an epoch 72 may be processed individually while others may be combined and analyzed in superposition.

In certain embodiments, a feature expansion module 84 may process a learning epoch 72 with feature operators 88 utilizing multiple waveform analysis techniques including time-frequency expansion, feature coherence analysis, principal component analysis, separation analysis, or the like. For example, processing learning epochs 72 with feature operators 88 may include applying frequency weighting factors, phase weighing factors, amplitude weighting factors, selective superposition of signals 24, or the like. In selected embodiments, processing learning epochs 72 with feature operators 88 may also include comparing spacial pattern, signal 24 shape, area under the curve of selected signals 24, or the like.

During processing by a feature operator 88, each learning epoch 72 may be decomposed into feature segments 92 in an extended phase space representing space, time, frequency, phase, or the like. The feature segments 92 pertaining to a selected epoch 72 may be collected to generate 94 a feature map 96. For example, in the illustrated embodiments of FIGS. 7 and 8, two feature operators 88 may expand an epoch 72. The first feature operator 88a may expand the epoch 72 into three time segments 98. The second feature operator 88b may expand each time segment 96 into twelve frequency bands 100.

The first and second operators 88a, 88b may expand the epoch 72 into time segments 98 and frequency bands 100 by any suitable method. For example, in the illustrated embodiments of FIGS. 7 and 8, a Gaussian weighting 102 may be used to define the bounds of the time segments 98 and frequency bands 100. The Gaussian weighting 102a of the first feature operator 88a may be defined in terms of a central time 104 and a time width 106. If desired, the time width 106 may represent the location where the weighting of the Gaussian distribution 102a is half the maximum weighting. Similarly, the Gaussian weighting 102b of the second feature operator 88b may be defined in terms of a central frequency 108 and a frequency width 110. If desired, the frequency width 110 may also represent the location where the weighting of the Gaussian distribution 102b is half the maximum weighting.

A feature map 96 may be generated 94 in any suitable manner. In the illustrated embodiment of FIG. 9, rows 112 may represent the various frequency bands 100 into which the epoch 72 was expanded. Columns 114 may represent the various time segments 98 into which the epoch 72 was expanded. Thus, each feature segment 92 may be charted according to its central frequency 108 and central time 104.

Once completed, a feature map 96 may be forwarded to a weighting module 116. Within a weighting module 116, a weight table 118 may be generated 120. A weight table 118 and accompanying weights 122 may be based on some manipulation of the signal data 24, 26 of an epoch 72 that will tend to self-neutralize. For example, certain resonance frequencies may occur at a frequency higher or lower than that of the background noise. Thus, shifting signal data 24, 26 slightly forward or backward within an epoch 72 and adding or multiplying the signal data 24, 26 together may provide enhancement of certain features 90, while minimizing others relative thereto.

As in the illustrated embodiment of FIG. 10, a weight table 118 contains a value of weight 122 for each feature segment 92 contained within a feature map 96. The weights 122 are arranged within the weight table 118 according to the feature segments 92 to which they apply. That is, the weights become coefficients. For example, the weight 122a contained in the first row and first column of the weight table 118 corresponds to the feature segment 92a in the first row and first column of the feature map 96. The weights 122 illustrated in FIG. 10 determine contributions or emphasize certain feature segments 92 while minimizing or virtually eliminating the effect of others.

In certain embodiments, upon leaving a weighting module 116, feature segments 92 may enter a consolidation module 124. In certain embodiments, the consolidation module 124 may apply 126 the weight table 118 to the feature map 96. Additionally, a consolidation module 124 may act to compile what was previously separated by the feature expansion module 84. For example, if an epoch 72 was expanded into feature segments 92 in the feature expansion module 84, then the consolidation module 124 may collect the feature segments 92 in an effort to form a feature 90.

A consolidation module 124 may consolidate feature segments 92 by any suitable method or mathematical manipulation. In certain embodiments, consolidation may include superposition 128 of the feature segments 92. This can be a weighted sum of values. If the feature operators 88 and weights 122 were effective, when the feature segments 92 are assembled back together (e.g. added, consolidated), a feature 90 (e.g. a non-random shape of a waveform) unique to the state of the epoch 72 (and not existing when that state does not exist) may appear.

In the embodiments of FIGS. 11 and 12, example learning epochs 72a, 72b corresponding to mutually exclusive states A and B are illustrated. Both epochs 72a, 72b may contain a signal 24 appearing to be random. After processing by one or more effective feature operators 88 and weights 122, a feature 90 corresponding to one state (A or B) and not the other (B or A) may be generated. In certain embodiments, recognizable, non-random patterns 90 or features 90 may be generated in epochs 72 corresponding to both states. In such cases, the feature operators 88 and weights 122 may still be considered effective so long as the feature 90 corresponding to state A is discernibly different from the feature 90 corresponding to state B.

In certain embodiments, before or after the feature segments 92 are superimposed 128, the consolidation module 124 may aggregate 130 the feature segments 92 or the resulting feature 90. Aggregation 130 may employ any method or mathematical manipulation directed to reducing the feature segments 92 or features 90 to a single numeric value characterizing the epoch 72. In certain embodiments, aggregation 130 may involve assigning a numerical value corresponding to the magnitude of the presence or non-presence of a particular feature 90.

In certain embodiments, after processing by a feature expansion module 84, a weighting module 116, and a consolidation module 124, a typing confidence module 132 may evaluate the ability of the various feature operators 88, weights 122, or the like to generate or extract features 90 that reliably segregate epochs 72 according to their state. Evaluation of the processing may be accomplished in any suitable manner.

In one embodiment, the assigned numerical values corresponding to each epoch 72 may be plotted. A distribution 134 of epochs 72 corresponding to state A may be compared to a distribution 136 of epochs 72 corresponding to state B. If desired, an optimal threshold value 138 that best divides the two distributions 134, 136 may be selected. The percentage of epochs 72 corresponding to state A falling on the correct side of the threshold value 138 may be calculated. Similarly, the percentage of epochs 72 corresponding to state B falling on the correct side of the threshold value 138 may be calculated. If the calculated percentages surpass a selected level of statistical significance, the processing may be considered effective. The learning system 76 may continue to iterate through various feature operators 88 and weights 122 until an optimal procedure or formula for segregating epochs 72 by state is determined.

In certain embodiments, the optimized procedure or formula for segregating epochs 72 by state may be forwarded to a separation key 80. For example, as illustrated in FIG. 13, a separation key 80 may outline the feature operators 88a, 88b successfully and reliably applied to generate a feature map 96. The separation key 80 may indicate the weights 122 successfully applied to the feature segments 92. A separation key 80 may also contain the optimal threshold value 138, superposition 130 procedure, aggregation 130 procedure, or the like that were found by the learning system 76 to be the most effective. In general, a separation key 80 contain anything learned by the learning system 76.

It may be noted that the portion of the separation key 80 illustrated in FIG. 13 has been found by an event contrast stacker 64 in accordance with the present invention to be effective in segregating portions of a signal 24 pertaining to geological formations 19 containing sand from portions of a signal 24 pertaining to geological formations 19 containing little or no sand. That is, by expanding an epoch 68 into the twelve noted frequency bands 100 and three noted time segments 98 and applying the noted weights 122, a feature 90 corresponding to the presence of absence of sand may be generated.

Figure 14:
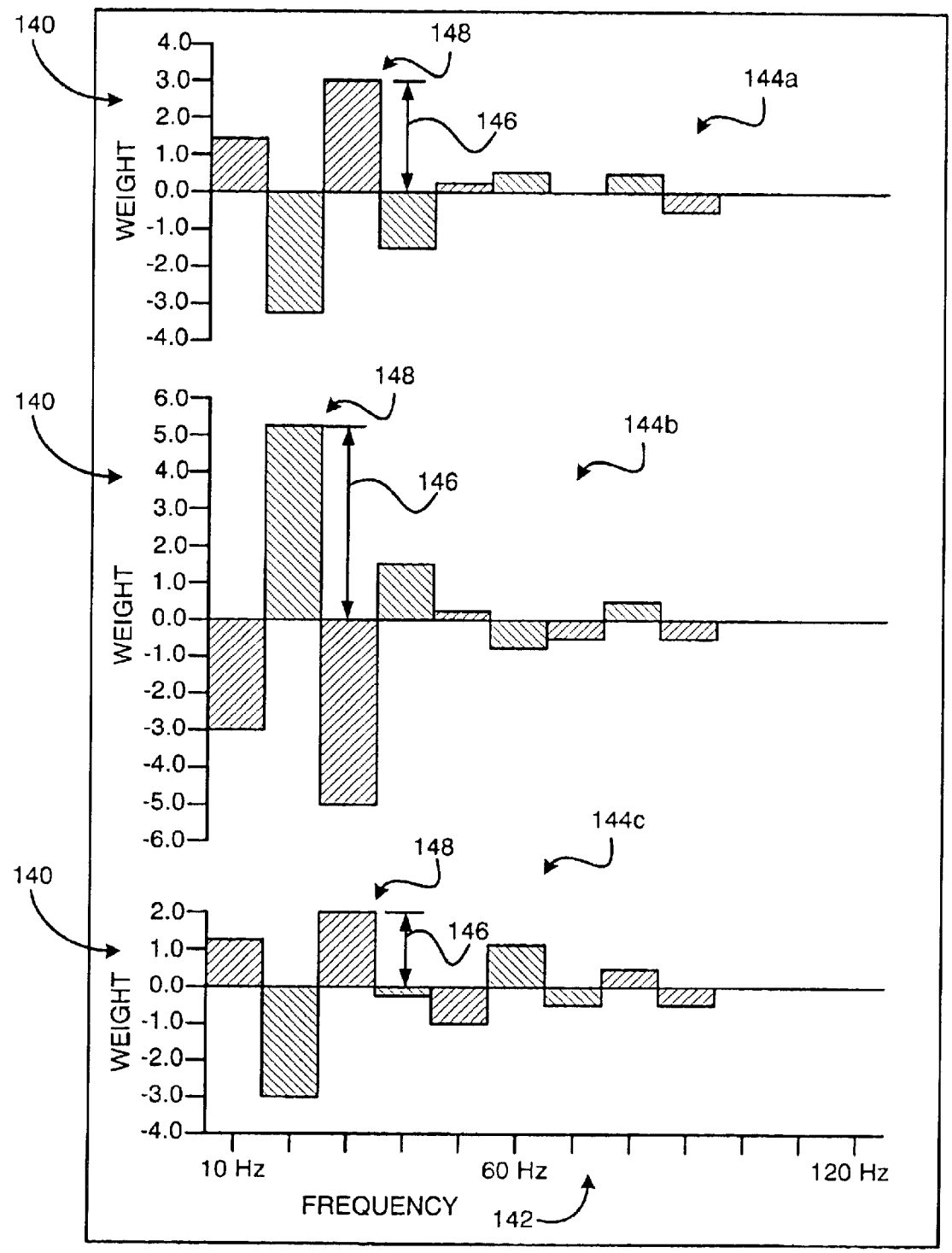
FIG. 14 is a graph of the separation key of FIG. 13.

Referring to FIG. 14, a separation key 80 may be presented graphically, if desired. For example, a vertical axis 140 may represent the weighting 122. A horizontal axis 142 may represent the frequency bands 100. Each graph 144a, 144b, 144c may represent one of the various time segments 98. A height 146 applied to a column 148 for each frequency band 100 may equal the weight 122 to be applied to that frequency band 100 for that time segment 98. FIG. 14 is arranged to be a graphical representation of the separation key 80 of FIG. 13.

Figure 15:
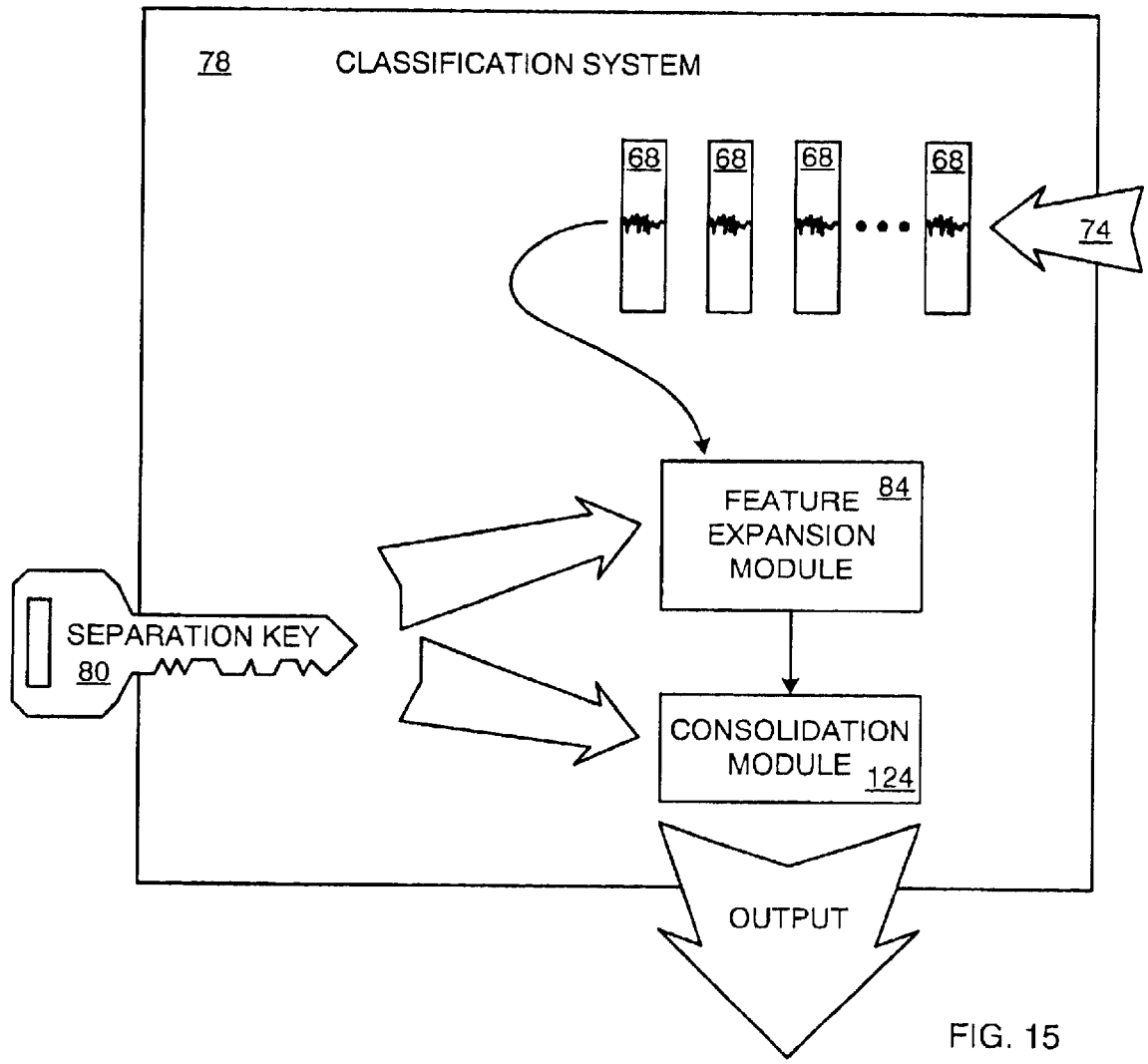
FIG. 15 is a schematic block diagram of an embodiment of a classification system from an event contrast stacker in accordance with the present invention.

Referring to FIG. 15, the learning system 76, once completed, may forward the separation key 80 to the classification system 78. The classification system 78 may receive and process classification epochs 74 in accordance with the procedures contained within the separation key 80.

In typical embodiments, the classification epochs 74 may be different from the learning epochs 72. Thus, the classification system 78 may test the separation key 80 on epochs 74 that the event contrast stacker has never "evaluated" to provide a more rigorous tester validation. If the state of each epoch is known, the process is a validation. If not, classification epochs 74 are prediction outputs for use. Additionally, the number of classification epochs 74 may be greater than the number of learning epochs 72. Classification epochs 74 may or may not be provided with a label 70 indicating the state of the geological formation 19 from which they were collected. During evaluation of a separation key 80, labels 70 containing state information may be helpful in comparing actual state segregation against state segregation generated by the separation key 80. Once a separation key 80 has been evaluated and proven reliable, any epoch 74 corresponding to geological formations 19 of unknown state may be received and processed by the classification system 78.

In certain embodiments, similar to a learning system 76, a classification system 78 may contain a feature expansion module 84 and a consolidation module 124. Unlike a learning system 76, however, a classification system 78 need not iterate through various procedures to collect the most effective feature operators 88, weights 122, superposition 128 procedures, aggregation 130 procedures, optimal threshold value 138, or the like. A classification system 78 in accordance with the present invention applies the feature operators 88, weights 122, superposition procedures 128, aggregation procedures 130, optimal threshold value 138, or the like that are provided in the separation key 80.

Accordingly, unlike the feature expansion module 84 of the of the learning system 76, the feature expansion module 84 of the classification system 78 does not apply a multitude of feature operators 88 to expand the epochs 74. The feature expansion module 84 of the classification system 78 simply applies the effective feature operators 88 delivered thereto as part of the separation key 80.

In selected embodiments, a weighting module 116 need not be included in a classification system 78. A consolidation module 124 of the classification system 78 may apply the weight table 118 contained in the separation key 80. Similarly, the consolidation module may apply the superposition procedure 128 and aggregation procedure 130 provided in the separation key 80. Upon completion of processing by the consolidation module 124, the resulting data may be passed to an output generator 82 to be converted into useful and easily accessible information.

Figure 16:
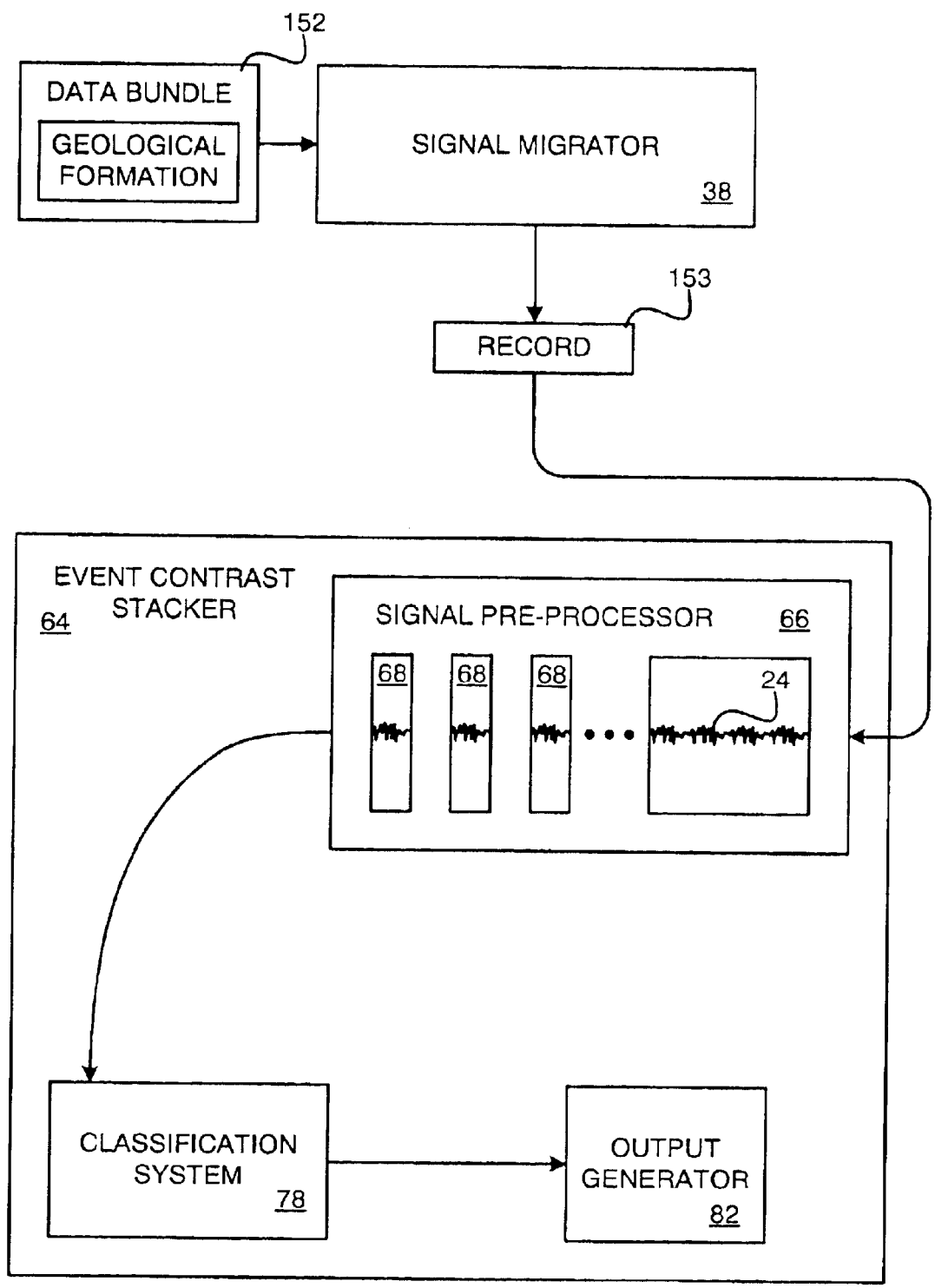
FIG. 16 is an alternative embodiment of an event contrast stacker in accordance with the present invention.
Figure 17:
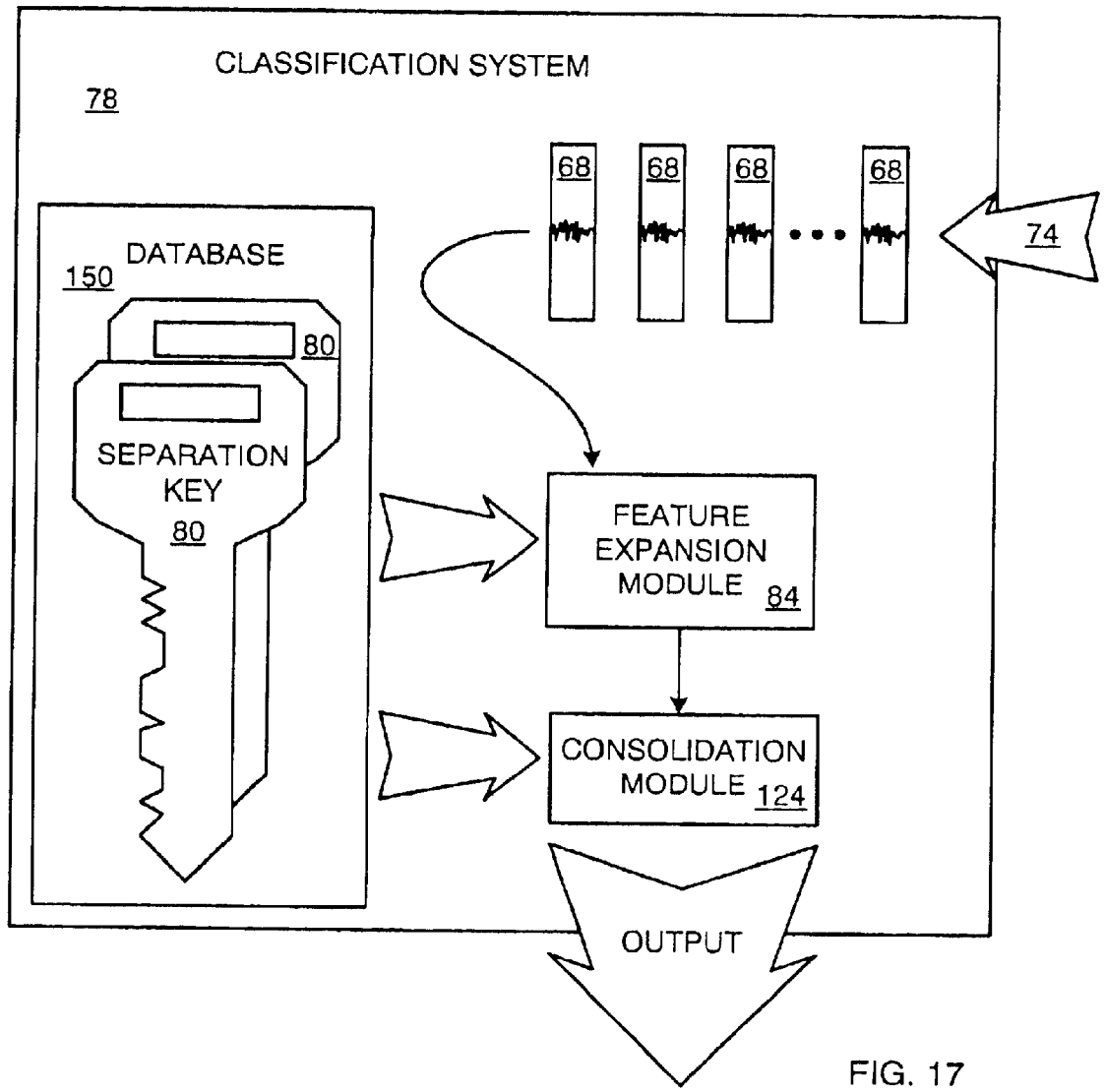
FIG. 17 is a schematic block diagram of an alternative embodiment of a classification system from an event contrast stacker in accordance with the present invention.

Referring to FIGS. 16 and 17, in certain applications, after sufficient confidence is developed in a particular separation key 80, it may not be necessary to enter the learning system 76 every time a new signal 24 is classified. Thus, an event contrast stacker 64 may be formed without a learning system 76. In such embodiments, a proven separation key 80 may be coded within the classification system 78.

For example, once a separation key 80 is generated for distinguishing between geological formations 19 containing oil above a desired production level and geological formations with no oil or with oil below a desired production level, a data bundle 152 contain signals 24 from a geological formation 19 having an unknown state may be analyzed. If desired, the data bundle 152 may be processed before entering an event contrast stacker 64. In one embodiment, the data bundle 152 may be processed by a signal migrator 38. A record 153 of the data bundle 152 may be generated. The record 153 may be forwarded to an event contrast stacker 64 and be divided by a signal pre-processor 66 into classification epochs 74. Since the state of the epochs 74 is unknown, the epochs 74 cannot be labeled therewith. However, each classification epoch 74 may be labeled with a coordinate (e.g. ordered triplet) or other designation indicating the location from which the epoch 74 originated.

Upon processing by a classification system 78 having the internal separation key 80, it may be determined whether the geological formation 19 corresponds more to a geological formations 19 containing oil above a desired production level or not, that is a geological formation with no oil or with oil below a desired production level. Accordingly, a user may determine which geological formations 19 are likely to produce oil as desired when tapped by a well.

As discussed hereinabove, certain embodiments of systems in accordance with the present invention may incorporate an event contrast stacker 64 into a single unit having a simple user interface. Such embodiments may be supplied with an internal database 150 containing various separation keys 80 for differentiating between hundreds or thousands of state pairs likely to be found in geological formations. A display and user interface may provide to a user the ability to select which separation key 80 is used. In an alternative embodiment, an event contrast stacker 64 may query the database 150 to find a separation key 80 most suited to a particular state comparison selected by a user.

An internal database 150 containing multiple separation keys 80 may also be supplied in addition to a learning system 76. An event contrast stacker 64 containing both an internal database 150 and a learning system 76 may more quickly analyze common states using separation keys 80 recorded in the database 150, while still providing the hardware and software to learn how to segregate additional states of geological formations 19. In selected embodiments, an event contrast stacker 64 in accordance with the present invention, may store a copy of every new separation key 80 generated in an internal database 150 for future reference. In such a manner, the event contrast stacker 64 may quickly build up a database 150 of effective feature operators 88, weights 122, and so forth.

Figure 18:
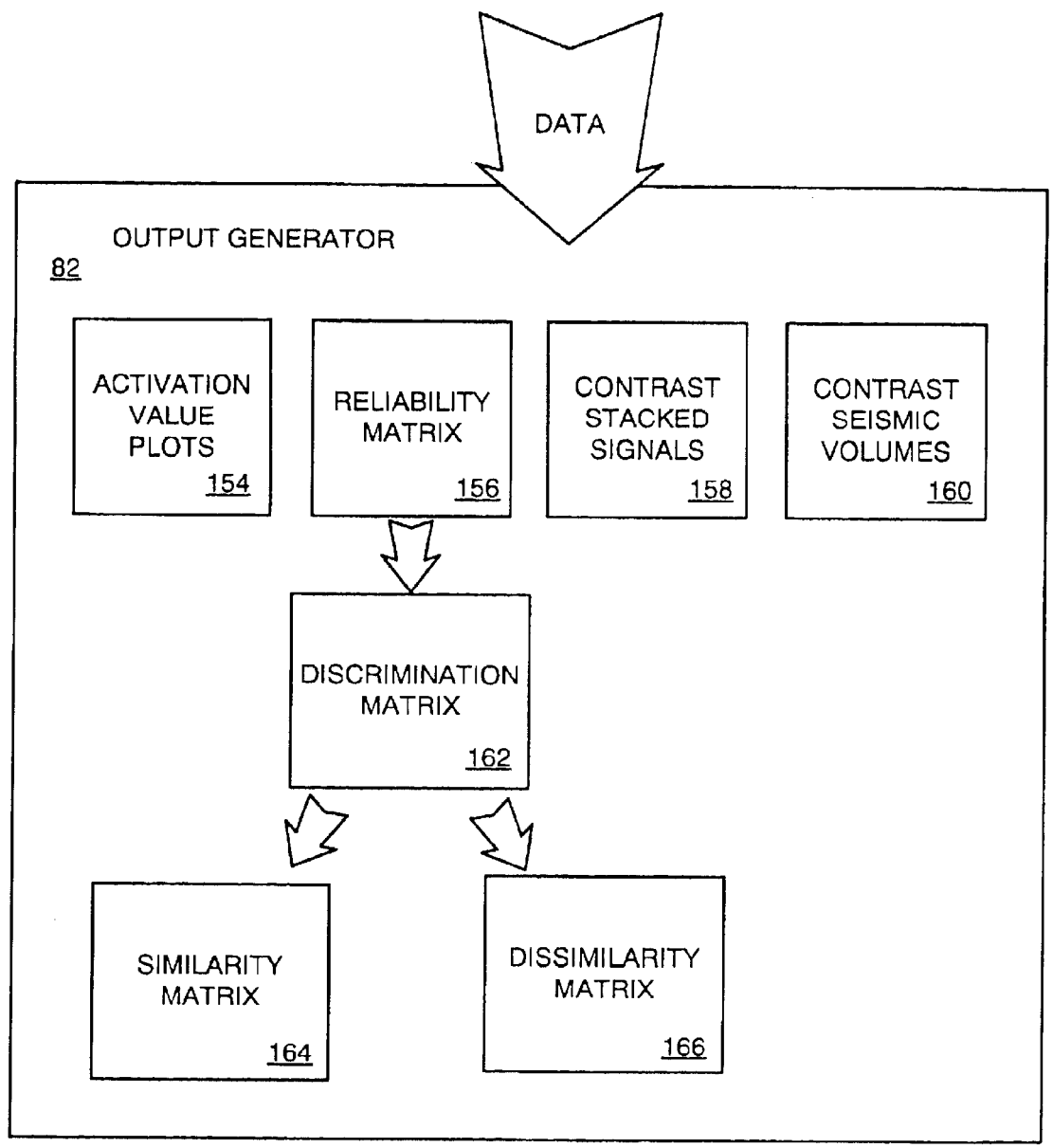
FIG. 18 is a schematic block diagram of an embodiment of an output generator from an event contrast stacker in accordance with the present invention.

Referring to FIG. 18, an event contrast stacker 64 in accordance with the present invention may present data in multiple useful formats. The following output formats are presented as exemplary models and are not to be interpreted as being restrictive of the available formats. For example, these formats may include activation value plots 154, reliability matrices 156, contrast stacked signals 158, contrast seismic volume 160, and so forth. Additionally, several useful matrices may be derived from a reliability matrix 156. These derivatives may include a discrimination accuracy matrix 162, similarity matrix 164, and dissimilarity matrix 166. Furthermore, in certain embodiments, it may be desirable to simply output a plot of the feature 90 produced by the event contrast stacker 64 before it is aggregated 130 to a numerical value.

Figure 19:
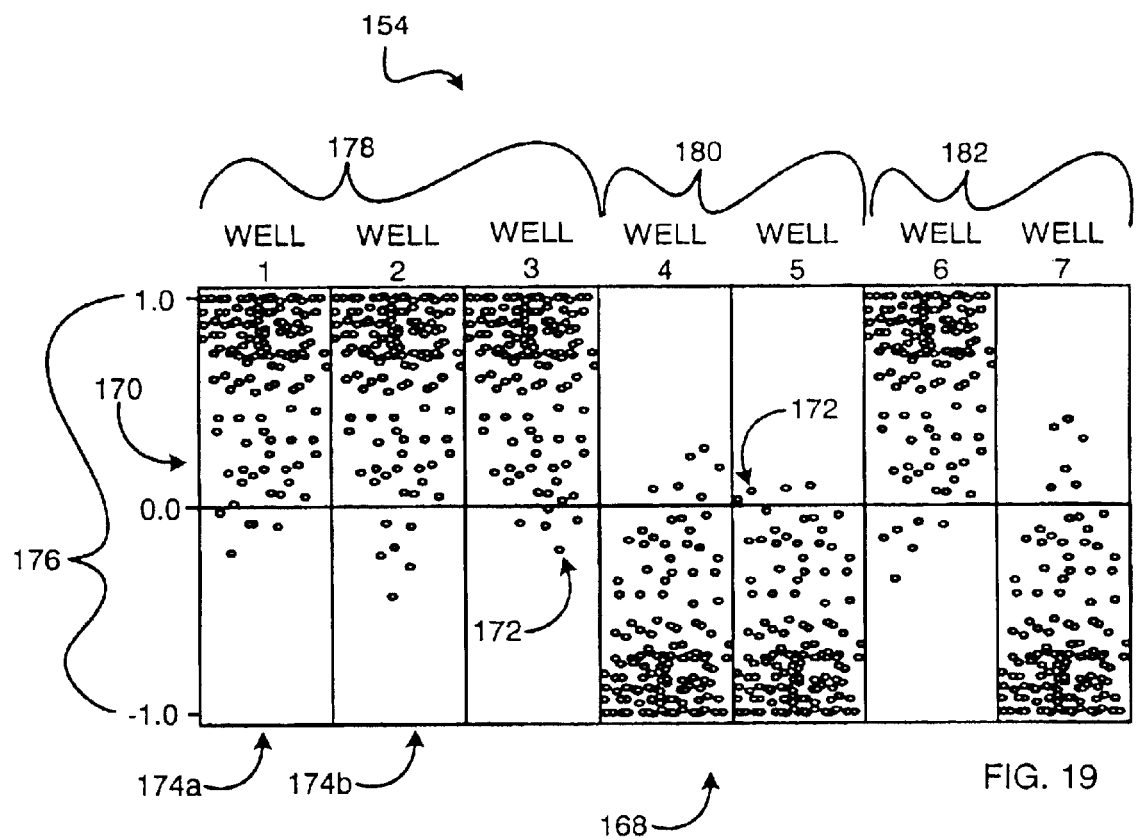
FIG. 19 is a graph of an activation value plot generated by an output generator in accordance with the present invention.

Referring to FIG. 19, an activation value plot 154 may have a spacing axis 168 and a magnitude axis 170. The spacing axis 168 may simply allow a plotted point 172 to be slightly spaced in the horizontal direction from neighboring plotted points 172. Thus, the plotted points 172 may be arranged to avoid entirely overlapping one another. The magnitude axis 170 may have a range 176 selected to illustrate a magnitude of the presence or non-presence of a particular distinguishing feature contained in each classified epoch 74.

In certain embodiments, the spacing axis 168 may also be divided according to geological formations 19. For example, a first section 174a of the spacing axis 168 may correspond to a first geological formation 19 penetrated by a first well. A second section 174b of the spacing axis 168 may correspond to a second geological formation 19 penetrated by a second well, and so on. The presence of a well may provide information concerning the state of the geological formation. For example, in the illustrated embodiment, wells one through three may be known gas producing wells 178, while wells four and five are known to be dry holes 180 or non-producing wells 180. Wells six and seven may be prospective wells 182 that are yet to be drilled.

To create an activation value plot 154, an assigned numerical value for each classified epoch 74 may be scaled or otherwise manipulated to fit in the magnitude range 176 of the plot 154. In one embodiment of a system in accordance with the present invention, the assigned numerical value is manipulated to fit within the range 176 from −1 to +1. The optimum threshold value 138 may be normalized to zero. Each small circle 172 or plotted point 172 may represent an epoch 74 of highly processed signal activity.

In the illustrated embodiment of FIG. 19, the producing wells 178 exhibit mostly positive (from 0 to +1) spectrum activation values. In contrast, the non-producing wells 180 exhibit mostly negative (from 0 to −1) spectrum activation values. The activation value plots 154 of prospective wells 182 may be compared to activation value plots for the producing and non-producing wells 178, 180. Well six shows a strong correlation to the producing wells 178. Thus, it may likely be profitable to drill well six. On the other hand, well seven shows a strong correlation to the non-producing wells 189. Thus, it is likely to be unprofitable to drill well seven.

The ability to non-invasively and accurately predict the state of a geological formation 19 may be profitable. Drilling a hydrocarbon well can be very expensive. By more accurately predicting which prospective wells are likely to produce, large sums of money may be saved by not drilling in unproductive sites.

Figure 20:
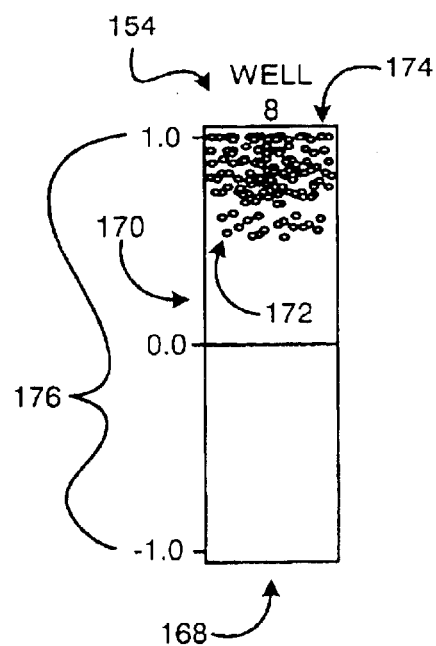
FIG. 20 is a graph of an alternative activation value plot generated by an output generator in accordance with the present invention.

Referring to FIG. 20, activation value plots 154 may be used to create a "fingerprint" corresponding to a particular state. Activation value plots 154 illustrate the relative probability that an epoch 74 corresponding to a particular state will have a particular magnitude. From the illustrated activation value plot 154, it can be seen that well eight has produced a dense concentration of plotted points 172 having values between 0.5 and 1.0 on the magnitude axis 170. While the plotted points 172 of FIG. 20 are similar to those shown in FIG. 19 for the producing wells 178, the point distribution 172 for the producing wells 178 in FIG. 19 is more spread out.

Thus, by examining the finger print illustrated in an activation value plot 154, a range of information may be extracted. For example, well eight is very different from the non-producing wells 180, but is not exactly like the producing wells 178. Further analysis may show that well eight is an exceptionally high producing gas well. Accordingly, variations in the activation value plots 154 may provide a spectrum of information.

Figure 21:
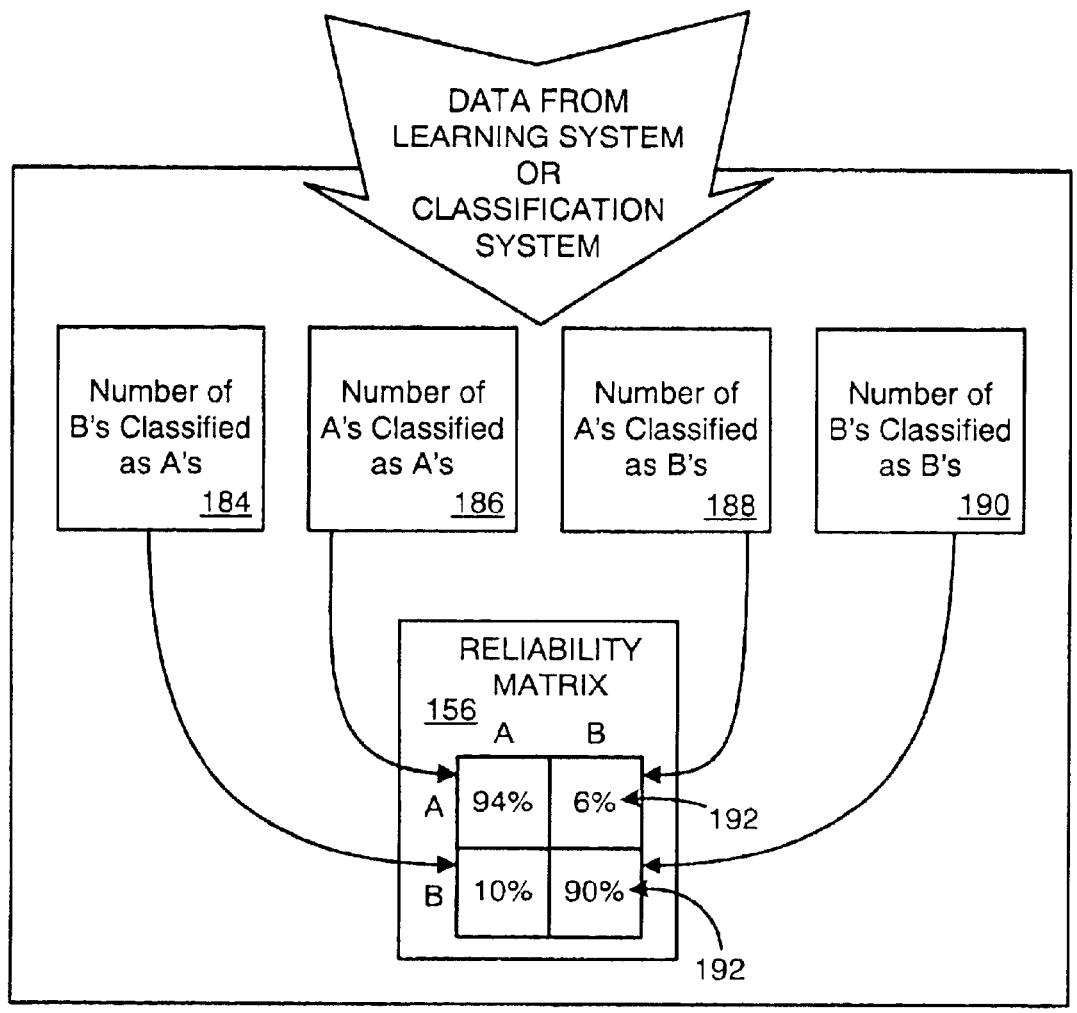
FIG. 21 is a schematic block diagram illustrating the formation of a reliability matrix by an output generator in accordance with the present invention.

Referring to FIG. 21, in certain embodiments of a system in accordance with the present invention, the classification accuracy of a particular separation key 80 may be determined by creating a reliability matrix 156. A reliability matrix 156 may be created by comparing the classification of an epoch 74 as corresponding to a particular state with the actual state associated with that epoch 74. For example, if a particular epoch 74 was classified as a "state A" epoch, then one of two things can be true. The epoch 74 can either correspond to a state A or state B. The same may be true for an epoch 74 classified as state B.

After comparing classification data against actual data, four numbers may be produced: the number 184 of state B epochs 74 erroneously classified as a state A epochs 74; the number 186 of state A epochs 74 correctly classified as state A epochs 74; the number 188 of state A epochs 74 erroneously classified as a state B epochs 74; and the number 190 of state B epochs 74 correctly classified as state B epochs 74. By dividing these numbers (i.e., the numbers indicated by the identifiers 184, 186, 188, 190) by the total number of actual epochs 74 related to their predicted state, accuracy or reliability percentages 192 may be calculated.

Reliability percentages 192 may be incorporated into a reliability matrix 156. For example, if 100 epochs 74 of state A where classified and 94 where correctly classified as corresponding to state A, then the AA (matrix notation) reliability percentage 192a would be 94%. That would leave 6 epochs 74 of state A that where erroneously classified as state B. The AB reliability percentage 192b would be 6%. The remaining BB and BA reliability percentages 192c, 192d may be calculated in a similar manner.

A reliability matrix 156 may provide the user a better understanding of the extent to which a particular classification may be trusted. In the illustrated example, a user may be quite comfortable that, using this particular separation key 80, a epoch 74 of state A will indeed be classified as a state A epoch 74 as the reliability matrix 156 indicates that 94% of all state A epochs 74 were correctly classified.

Referring to FIG. 22, multiple reliability matrices 156a, 156b, 156c, . . . , 156n may be used to generate a discrimination accuracy matrix 162. Reliability matrices 156 provide the probability that two states (A and B, B and C, C and D, or the like) will be classified correctly. A discrimination matrix 162, on the other hand, may provide information about how well a particular separation key 80 is able to differentiate several states.

For example, a particular reliability matrix 156b may state that when compared with state B, an event contrast stacker 64 may correctly classify 88% of all state A epochs 74. When compared with state A, that same event contrast stacker 64 may correctly classify 90% of all state B epochs 74. A total classification accuracy 194b of the event contrast stacker 64 with respect to states A and B may be determined by averaging the two correct reliability percentages 192. In the illustrated embodiment of FIG. 22, the generation of various total classification accuracies 194 is shown in a matrix notation 196 as well as a numeric example 198. In applications where the number of state A epochs 74 analyzed does not equal the number of state B epochs 74 analyzed, a total classification accuracy 194 may be determined by adjusting, such as by dividing the total number of correct classifications (regardless of state) by the total number of epochs 74 analyzed.

Once a total classification accuracy 194 has been generated for a particular pair of states, this value 194 may be inserted in the appropriate locations of the discrimination accuracy matrix 162. It may be noted that discrimination matrices 162 are symmetric, thereby reducing the number of calculations necessary to complete the matrix 162. Reliability matrices 156 may be generated and total classification accuracies 194 calculated using selected state pairs until the discrimination matrix 162 is complete.

A complete discrimination matrix 162 may provide the user with a comparison of the similarities of a variety of states. It may be noted that the diagonal 200 of the discrimination matrix 162 may often contain values near 50%. The diagonal 200 contains total classification accuracies 194 of a particular state compared against itself. As would be expected, an event contrast stacker 64 may not repeatably distinguish a given state from itself. Therefore, it is typically right half the time and wrong half the time.

Referring to FIG. 23, a discrimination matrix 162 may be converted to a dissimilarity matrix 166 by a dissimilarity transformation 202. Dissimilarity matrices 166 provide a method for comparing how different a particular state is from another state. As can be seen, the diagonal 200 contains low dissimilarity values. This is to be expected as states have a low (theoretically zero) dissimilarity with themselves.

Referring to FIG. 24, a discrimination matrix 162 may be converted to a similarity matrix 164 by a similarity transformation 204. As can be seen, the diagonal 200 contains high similarity values. This is to be expected as states are similar to themselves. Similarity matrices 164 may be particularly useful. A similarity matrix 164 enables a user to objectively calculate how similar a particular state is to another state. This comparison may have a profound impact on the ability of a user to predict and quantify states.

Figure 25:
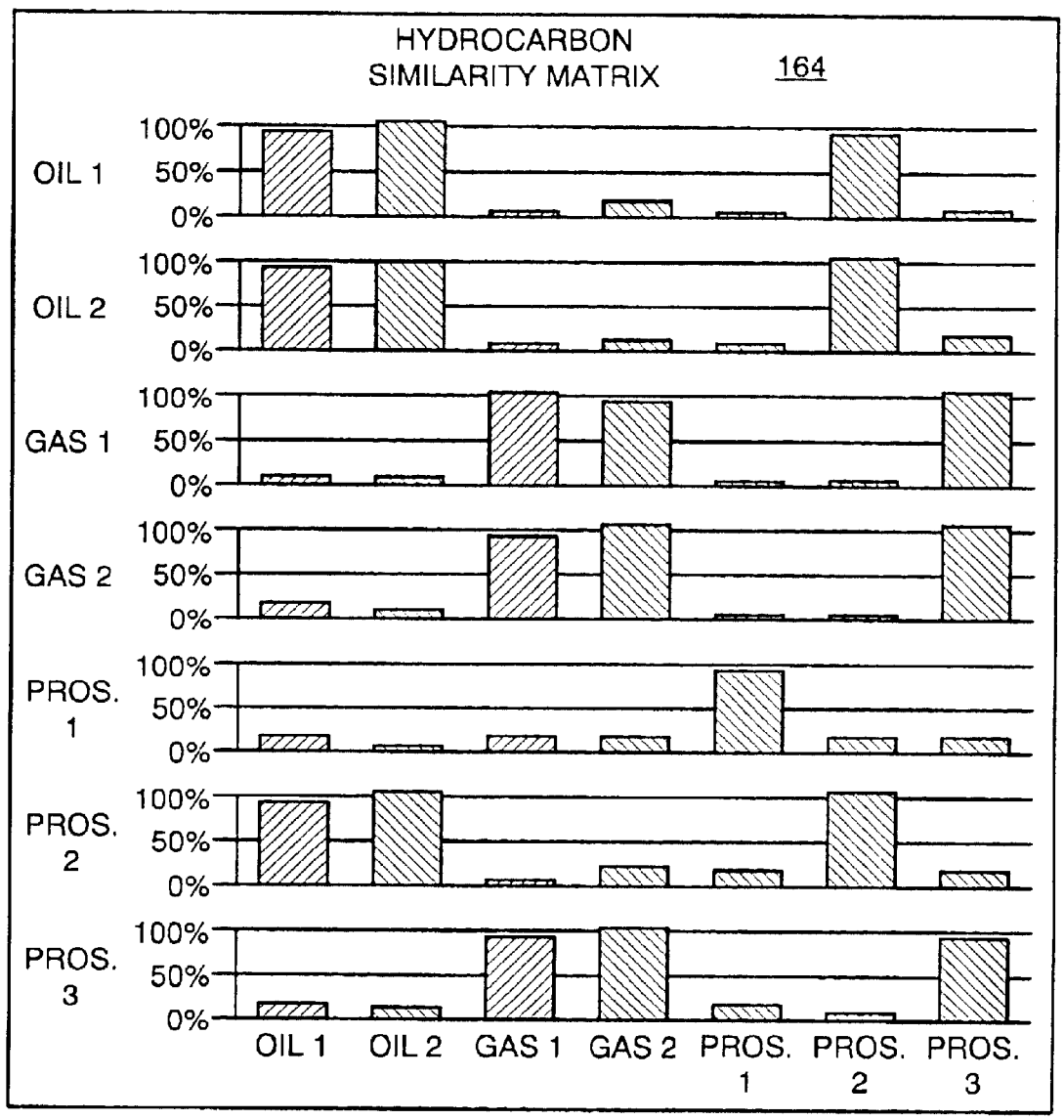
FIG. 25 is a schematic block diagram illustrating an alternative embodiment of a similarity matrix in accordance with the present invention.

Referring to FIG. 25, a similarity matrix 164 may be presented as a bar graph. The bar graph provides a visual representation of areas of similarity and dissimilarity between various geological formations 19 having various states. For example, in the illustrated embodiment, two geological formations 19 known to contain oil, two geological formations 19 known to contain gas, and three geological formations 19 having prospective well sites are compared. As expected, the geological formations 19 containing oil show a high similarity to one another. Similarly, the geological formations 19 containing gas show a high similarity to one another. The first prospective well shows no similarity to oil or gas. The second prospective well shows a similarity to oil. The third prospective well shows similarity to gas.

Figures 26, 27, 28:
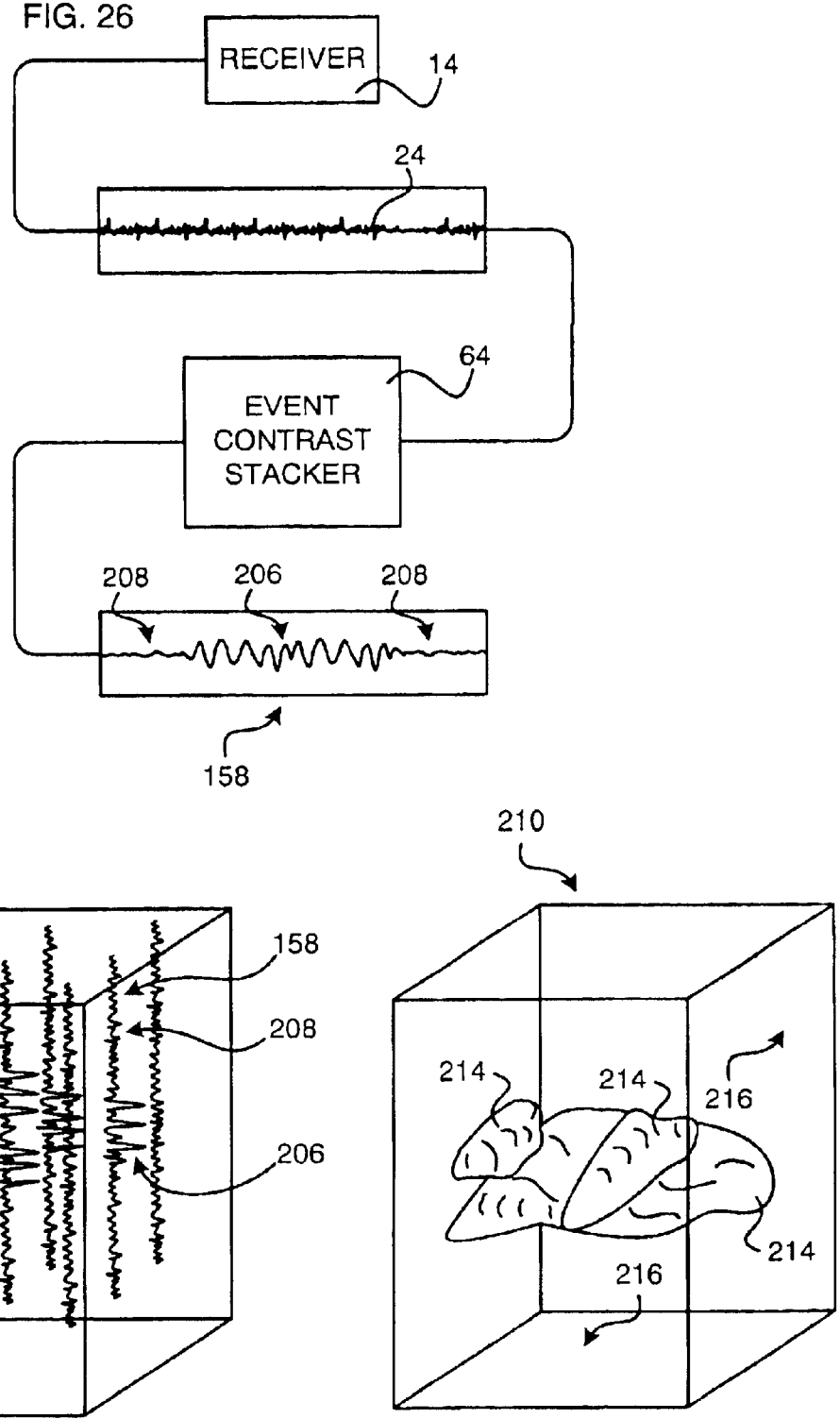
FIG. 26 is a schematic block diagram illustrating the formation of a contrast stacked signal by an event contrast stacker in accordance with the present invention.
FIG. 27 is a schematic diagram of a seismic contrast volume generated by an event contrast stacker in accordance with the present invention.
FIG. 28 is a schematic diagram of a three-dimensional image corresponding to the seismic contrast volume of FIG. 27 in accordance with the present invention.
Figure 29:
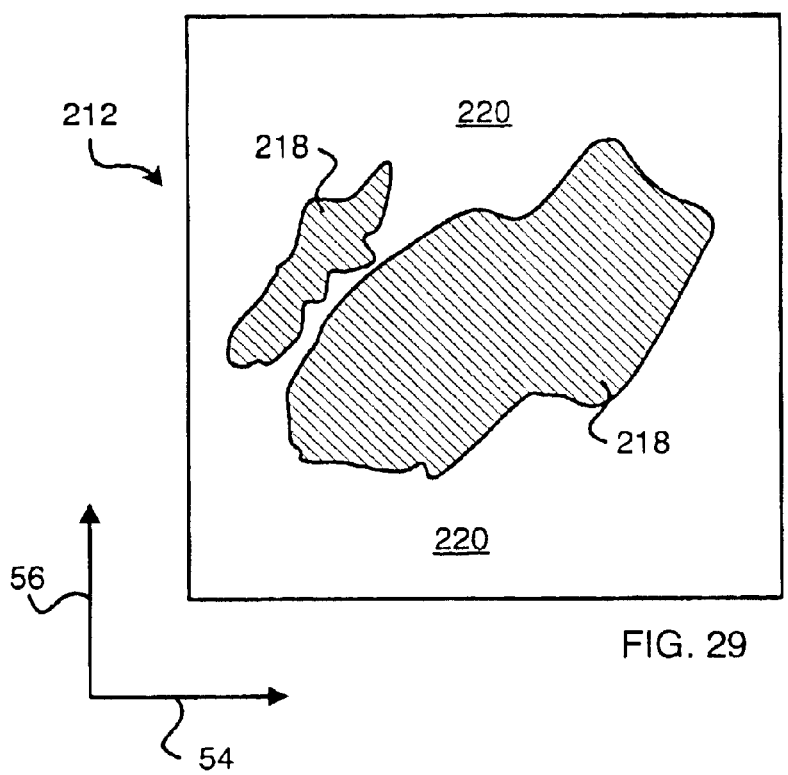
FIG. 29 is a schematic diagram of a two-dimensional, horizontal image corresponding to the seismic contrast volume of FIG. 27 in accordance with the present invention.
Figure 30:
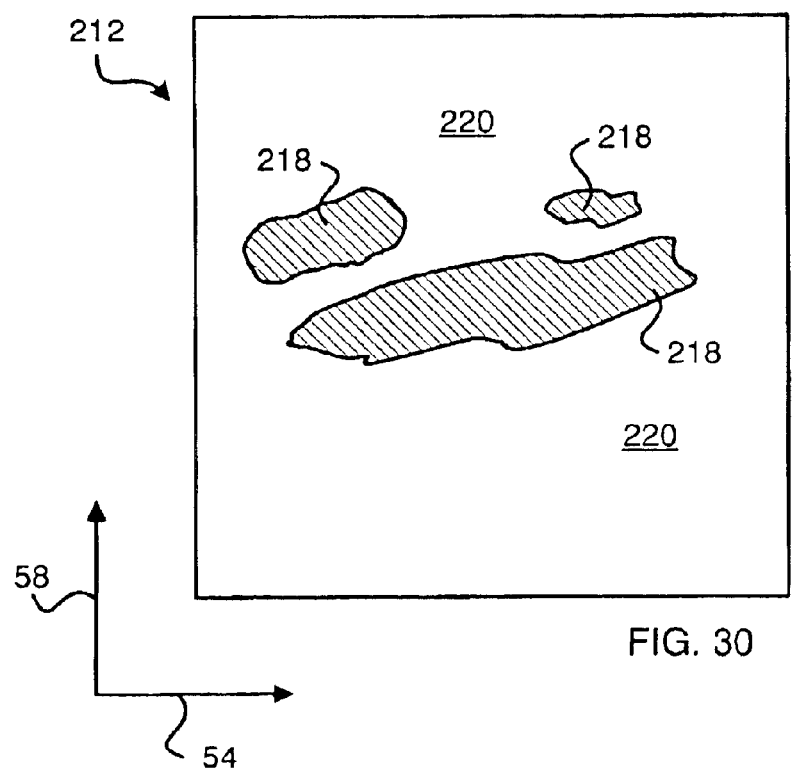
FIG. 30 is a schematic diagram of a two-dimensional vertical image corresponding to the seismic contrast volume of FIG. 27 in accordance with the present invention.
Figure 33:
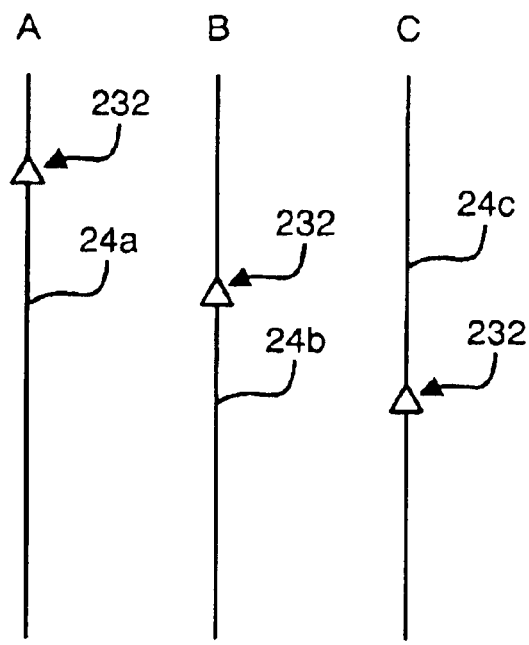
FIG. 33 is a schematic diagram of selected seismic traces containing a common event.
Figure 34:
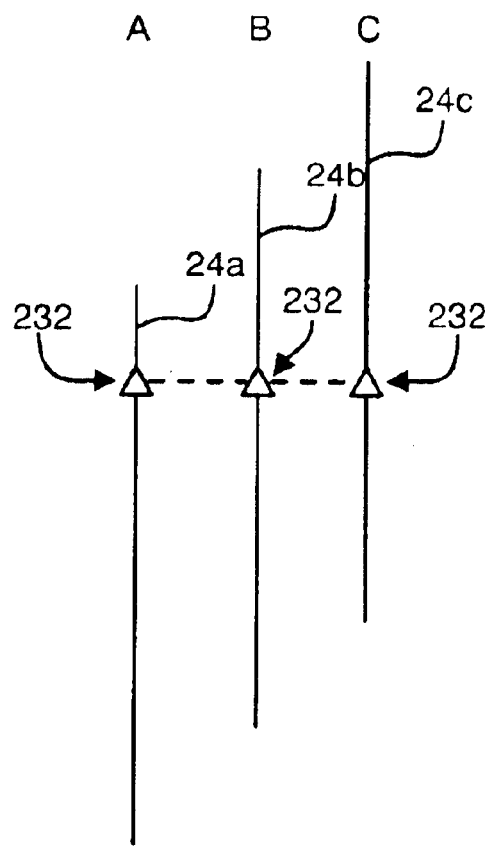
FIG. 34 is a schematic diagram of the selected seismic traces of FIG. 33 migrated in accordance with the present invention to align common events.
Figure 35:
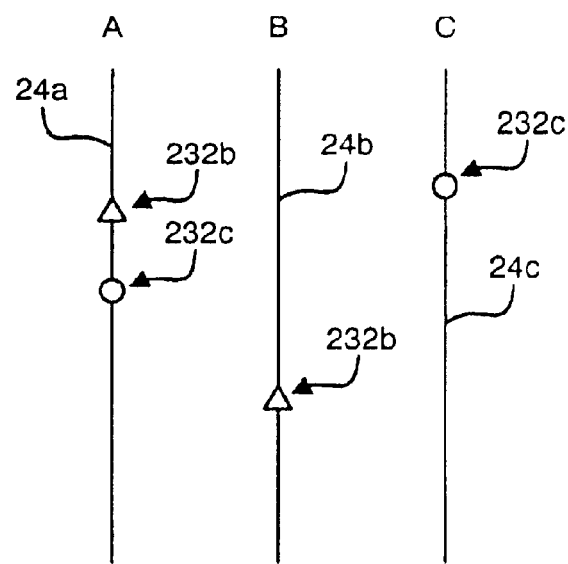
FIG. 35 is a schematic diagram of selected seismic traces containing various events.
Figure 36:
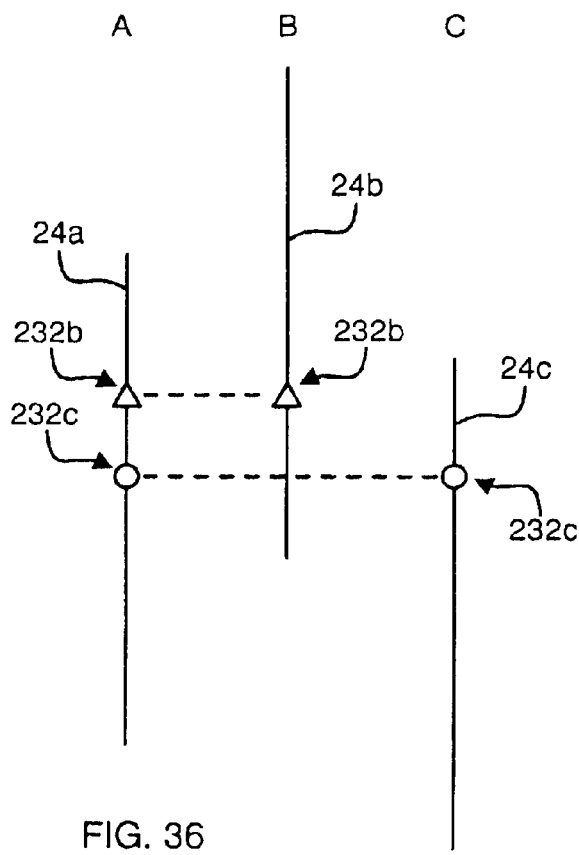
FIG. 36 is a schematic diagram of the selected seismic traces of FIG. 35 migrated in accordance with the present invention to align the various events.

Referring to FIG. 26, an output generator 82 of an event contrast stacker 64 in accordance with the present invention may output information in the form of a contrast stacked signal 158 or contrast stacked trace 158. As discussed hereinabove, in certain embodiments, an event contrast stacker 64 may receive a complex and apparently random signal 24. The event contrast stacker 64 may divided the signal 24 into epochs 68. Each epoch 68 may be processed by the event contrast stacker 64 in an effort to reveal features 90 (inherent characteristics indicating non-random information encoded within the signal 24) that correspond to a particular state of the formation 19 from which the signal 24 was collected.

Once the features 90 of each epoch 68 have been expanded, the epochs 68 may be reassembled in the order they were taken from the signal 24. This reassembly may result in the formation of a contrast stacked signal 158. That is, a signal 158 that is stacked, collected, summed, or otherwise processed in a manner to draw out contrasts between portions 206 of the signal 158 pertaining to state A and portions 208 of the signal 158 pertaining to state B.

Referring to FIGS. 27–30, if desired, a collection of contrast stacked signals 158 may be arranged in their proper relative locations in three-dimensional Euclidean space. A collection of properly positioned contrast stacked signals 158 may constitute a contrast seismic volume 160. In certain embodiments, a contrast seismic volume 160 may represent a map of a selected physical volume of a geological formation 19. The contrast seismic volume 160 may indicate locations corresponding to different states.

Various methods may be used to operate on a contrast seismic volume 160 and generate three dimension images 210 or two dimensional images 212 of a geological formation 19. In selected embodiments, three dimensional images 210 may be generated by interpolating between the collection of contrast stacked signals 158. The illustrated embodiment of FIG. 28 provides a three dimension image 210 of volumes 214 corresponding to state A and volumes 216 corresponding to state B. In certain embodiments, volumes 214 corresponding to state A may represent an oil deposit that will produce oil above a selected threshold rate, while volumes 216 corresponding to state B may be formations that will not produce oil at a rate above a selected threshold value.

As stated hereinabove, a contrast seismic volume 160 may be used to generate two dimensional images 212. In the illustrated embodiment of FIG. 29, a horizontal, two dimensional slice 212 provides views of regions 218 corresponding to state A and regions 220 corresponding to state B at a certain physical depth. In the illustrated embodiment of FIG. 30, a vertical, two dimensional slice 212 provides additional views of regions 218 corresponding to state A and regions 220 corresponding to state B at a certain distance.

Referring to FIGS. 31 and 32, in certain embodiments, it may be desirable to divide a contrast seismic volume 160 into various sub-volumes 222. The size or number of the sub-volumes 222 may vary according to the desired resolution. In selected embodiments, each sub-volume 222 may be labeled with a number 224 indicating the correspondence of that sub-volume 222 to a particular state. The resulting collection of numbered sub-volumes 222 may form a numeric plot 226.

The number 224 may be selected by quantifying the presence or absence of a feature 90 in a portion 206, 208 of the contrast stacked signal 158 contained within the sub-volume 222. If desired, the number 224 may be the numerical value assigned the portion 206, 208 in the aggregation 130 process. In selected embodiments, more than one contrast stacked signal 158 may pass through a sub-volume 222. In such situations, the number 224 may be selected to represent the presence or absence of a feature 90 in selected portions 206, 208 of the various contrast stacked signals 158 contained within the sub-volume 222. In one embodiment, the number 224 may be an average of the numerical value assigned to the selected portions 206, 208 in the aggregation 130 process.

In selected embodiments, each sub-volume 222 may have a color 228 applied thereto. The color 228 may provide a visual key indicating the correspondence of that sub-volume 222 to a particular state of interest. The resulting collection of colored sub-volumes 222 may be combined to form a color plot 230. For example, in one embodiment, the various colors 228 applied to the sub-volumes 222 may represent a spectrum or scale of color. Sub-volumes 222 containing portions 206, 208 of the contrast stacked signal 158 representing a high probability of the desired state, represented by the high incidence of a particular feature 90, may be assigned a color 228 at one end of the selected color spectrum. Conversely, sub-volumes 222 containing portions 206, 208 of the contrast stacked signal 158 representing a low incidence of the particular feature 90 may be assigned a color 228 at the other end of the color spectrum or other contrasting color. Sub-volumes 222 containing portions 206, 208 of the contrast stacked signal 158 representing an intermediate incidence of the particular feature 90 may be assigned a corresponding color 228 from the interior of the color spectrum.

Various colors 228 or color spectra may be applied to any output generated by an output generator 82 in accordance with the present invention. For example, in addition to the color plots 230 described hereinabove, colors 228 and color spectra may be applied to activation value plots 154, reliability matrices 156, contrast stacked signals 158, contrast seismic volumes 160, three dimensional images 210, two dimensional images 212, or the like. Colors 228 and color spectra may be used to immediately communicate information to a viewer regarding the degrees of presence or absence of a particular state within a geological formation 19.

In selected embodiments, traces 24 that are migrated may be combined with color coded contrast stacker signals 158. The end result may be a combination of information available in seismic traces 24 before processing by an event contrast stacker 64 and information obtained after processing by an event contrast stacker 64. The color coded contrast stacked signals 158 may enhance the seismic traces 24 and indicate what locations in the seismic traces 24 represent a particular state of the geological formation.

In certain embodiments, activation value plots 154, reliability matrices 156, contrast stacked signals 158, contrast seismic volumes 160, three dimensional images 210, two dimensional images 212, numeric plots 226, color plots 230, or the like may be used to quantify the portions 206, 208, volumes 214, 216, and regions 218, 220 corresponding to different states. For example, if state A represents the presence of an oil deposit in a geological formation 19, a three dimensional image 219 may provide the ability to quantifying the number of barrels of oil that may be contained in a volume 214 corresponding to state A.

Additionally, signals 24 may be collected from a particular geological formation 19 at different times. By using the methods and structures in accordance with the present invention, the portions 206, 208, volumes 214, 216, and regions 218, 220 pertaining to a particular state may be calculated for each time the signals 24 are collected. The portions 206, 208, volumes 214, 216, and regions 218, 220 may be compared between different collections of signals 24 to determine how the geological formation 19 is changing. For example, the volume 214 corresponding to the presence of an oil deposit may be quantified in a first year. In subsequent years, such as after each year of pumping, signals 24 may again be collected and the volume 214 corresponding to the presence of an oil deposit may again be quantified. By comparing the quantities, the impact of pumping on the oil deposit may be evaluated.

Referring to FIGS. 33–36, in certain embodiments, an event contrast stacker 64 may migrate or to assist in migrating seismic traces 24. As discussed hereinabove, migration is an attempt to locate the source of signals 24 that have traveled large distances (e.g. long times). One of the techniques that may be used to migrate seismic traces is event aligning. An event 232 may be defined as a section of a seismic trace 24 corresponding to the reflected wave 22 caused by a particular reflector 20. A seismic trace 24 is, in reality, a collection of events 232 represented by a shape of a waveform, obscured by noise.

In certain applications, selected traces 24a, 24b, 24c may contain common events 232. Common events 232 may be defined as reflected waves 22 originating from a common reflector 20. By locating waveshapes or recognizable common events 232 in multiple traces 24a, 24b, 24c, the traces 24 may be adjusted until common events 232 are aligned, such as in time. Aligning may facilitate piecing together the various traces 24 to form a collection of fully migrated traces 24.

An event contrast stacker 64 in accordance with the present invention may be used to compare signals 24 and identify signals 24a having an information content that is either more readily exposed or simply stronger than others. Signals 24a having such high information content and visibility may then be used for facilitating processing of other signals 24b, 24c. For example, a plurality of events 232b, 232c may be identified along a signal 24a of high information visibility. Other low information signals 24b, 24c may contain one of the plurality of events 232. It may be difficult to align two low information signals 24b, 24c if a common event 232 is not readily located. However, the high information signal 24a may contain an event 232b in common with a low information signal 24b as well as an event 232c from another low information signal 24c. Thus, using the high visibility or simply high information signal 24a, the low information signals 24b, 24c may be aligned with respect to one another.

The following examples will illustrate the invention in further detail. It will be readily understood that the present descriptions of certain aspects of the invention, as generally described and illustrated in the Examples herein, are merely exemplary of embodiments of apparatus and methods in accordance with the present invention. Thus, the following more detailed description of certain embodiments of methods and formulations in accordance with the present invention, as represented in Examples I through IV, is not intended to limit the scope of the invention, as claimed, but is merely representative of possible embodiments and applications of the present invention.

EXAMPLE I

Referring to FIGS. 37–43, in the present example, signals 24 (post-stack gathers) were provided from a twenty square mile area of an operating oil field. The signals had previously been used to generate conventional seismic volumes illustrated in FIGS. 37 and 39. Twelve wells 30 were drilled based on the seismic volumes. As can be seen, all the wells 30 are positioned in areas 234 that the seismic volumes indicated are likely locations for oil.

Of the twelve bores 30 or wells 30, two resulted in oil wells 30a, 30b, two resulted in dry holes 30c, 30d, and two resulted in wet holes 30e, 30f (water filled). The states of the remaining six wells 30g, 30h, 30i, 30j, 30k, 30m were known to the owners of the oil field, but were withheld until processing in accordance with the present invention was completed.

Figures 41, 42:
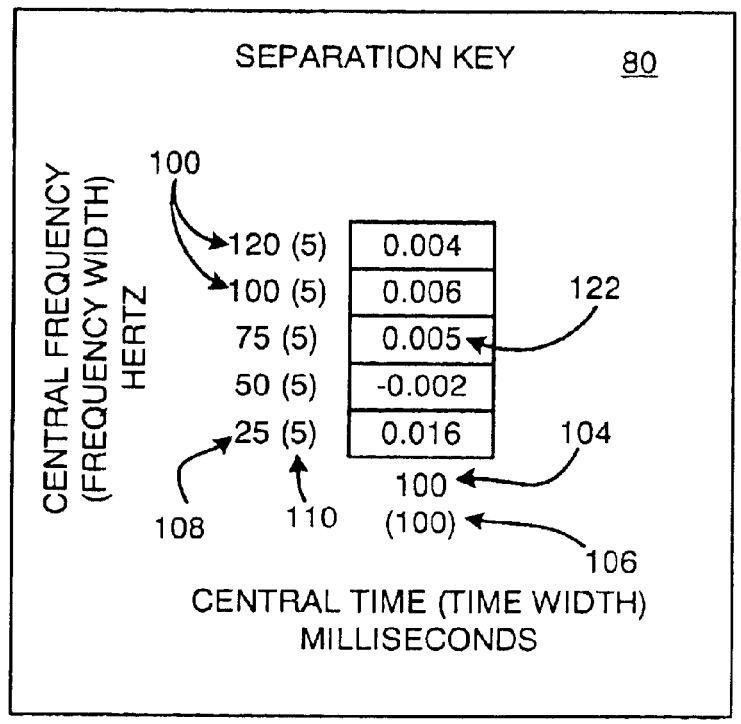
FIG. 41 is a table illustrating the status, time window examined, and number of traces processed in accordance with the present invention for each of the various wells drilled in the oil field.
FIG. 42 is a table illustrating a portion of a separation key found by an event contrast stacker in accordance with the present invention to be effective on seismic data collected from the oil field.

As illustrated in FIG. 41, selected signals 24 corresponding to each of the wells 30 were provided for processing. The number 236 of signals 24 provided for each well 30 ranged from 154 to 177. The signals 24 were processed by an event contrast stacker 64 in accordance with the present invention.

The area of interest, or pay horizon 62, of the oil field of the present example was located about 1.1 seconds from the surface 16. As a result, an epoch 68 was taken from each of the signals 24 in the range extending from 0.1 seconds before the pay horizon 62 to 0.1 seconds after the pay horizon 62. Thus, each epoch 68 represented 0.2 seconds (200 milliseconds) of a signal 24. Since the pay horizon 62 of the actual oil field did not remain at a constant depth, the exact location of the various epochs 68 varied for different wells 30. For example, the epochs 68 corresponding to well one 30a extended from time 0.976 to time 1.176 while the epochs 68 from well two 30b extended from time 0.964 to time 1.194.

The geological formation 19 containing well two 30b, an oil well, was considered an example of state A (i.e. an oil producing location). The geological formations 19 containing well three 30c, a dry hole, and well five 30e, a wet hole, were considered examples of state B (i.e. non oil producing locations). Epochs 68 corresponding to wells two 30b, three 30c, and five 30e were used as learning epochs 72 and processed by a learning system 76 in accordance with the present invention. Epochs 68 corresponding to wells one 30a, four 30d, and six 30f through twelve 30m were used as classification epochs 74 and processed by a classification system 78 in accordance with the present invention.

After processing the learning epochs 72, the learning system 76 produced a separation key 80 illustrated in part by FIG. 42. It was determined that each epoch 72 may be weighted in time space with a Gaussian distribution 102 centered at time 100 milliseconds (halfway though the epoch 72) with a time width 106 of 100 milliseconds. It was also determined that each epoch 72 may be divided in a frequency space into five frequency bands 100. The frequency bands 100 may be weighted with Gaussian distributions 102 centered at 25 Hz, 50 Hz, 75 Hz, 100 Hz, and 120 Hz, all with frequency widths 110 of 5 Hz. Weights 122 for the resulting feature segments 92 may be applied as illustrated.

The learning epochs 72 and the classification epochs 74 were processed by the classification system 78 using the separation key 80 developed by the learning system 76. Each epoch 68 was expanded into feature segments 92. The feature segments 92 corresponding to a particular epoch 68 were weighted, superimposed 128, and aggregated 130 to a numerical value. The numerical values were normalized and plotted in the activation value plot 154 of FIG. 43. Each processed epoch 68 is represented by a plotted point 172. Plotted points 172 between 0.0 and 1.0 indicate a correspondence to an oil producing state. Plotted points 172 between 0.0 and −1.0 indicate a correspondence to a non oil producing state.

Figure 43:
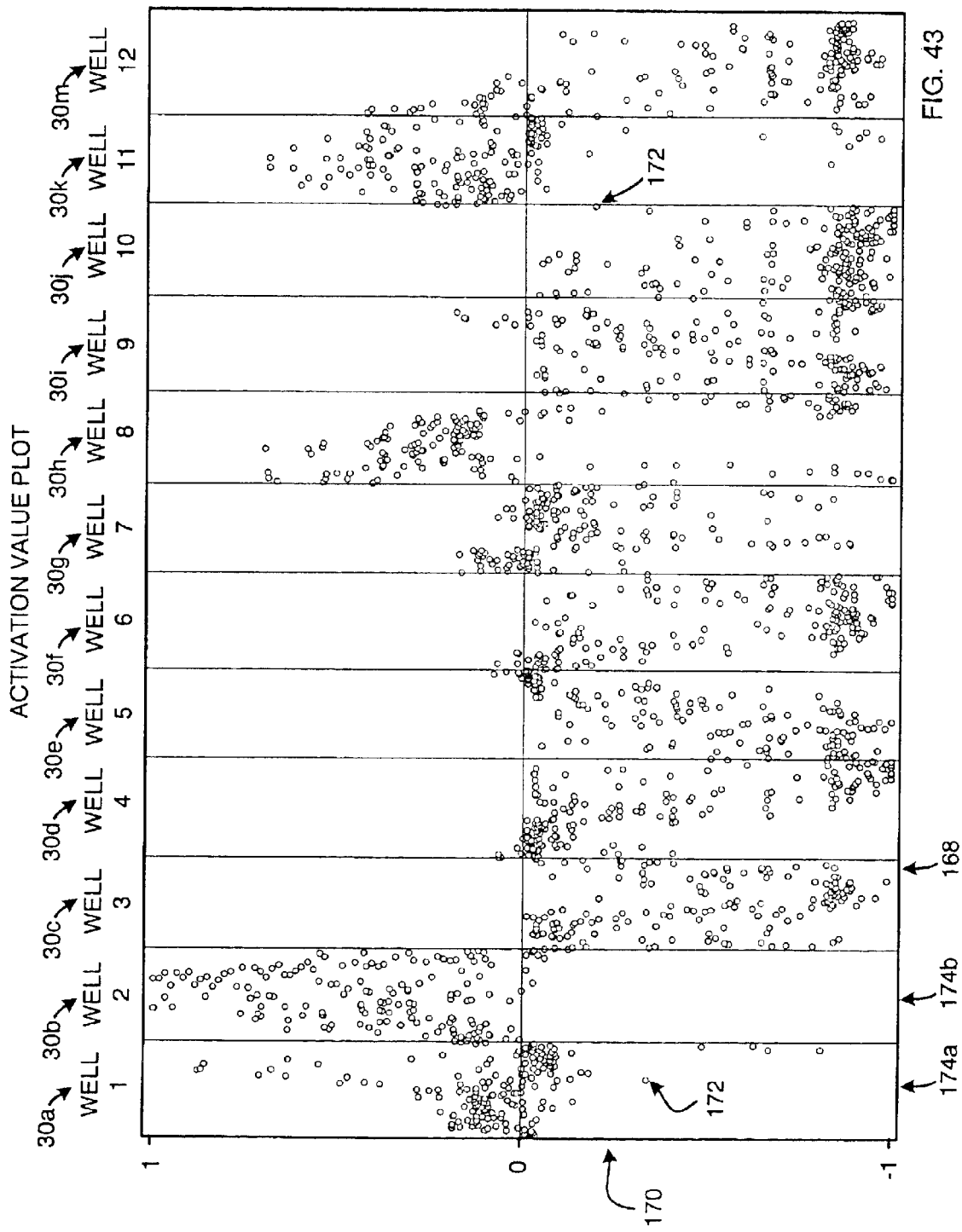
FIG. 43 is a graph of an activation value plot generated by an event contrast stacker in accordance with the present invention from seismic data collected from the oil field.

As seen in FIG. 43, wells one 30a and two 30b were properly classified as oil wells. Wells three 30c though six 30f were properly classified as non-producing wells. Of the unknown test wells (i.e. wells seven 30g though twelve 30m), wells eight 30h and eleven 30k were classified as oil wells, while wells seven 30g, nine 30i, ten 30j, and twelve 30m were classified as non-producing wells. Upon viewing the data, the oil field owners confirmed that wells eight 30h and eleven 30k were indeed oil wells and wells seven 30g, nine 30i, ten 30j, and twelve 30m were indeed non producing wells. Thus, the processing of the event contrast stacker 64 in accordance with the present invention was validated.

A horizontal, two dimensional slice 212 of the oil field as processed in accordance with the present invention is illustrated in FIG. 38. A vertical, two-dimensional slice 212 of the oil field as processed in accordance with the present invention is illustrated in FIG. 40. As can be seen in FIGS. 38 and 40, all the oil wells 30a, 30b, 30h, 30k are positioned in areas 238 that an event contrast stacker 64 in accordance with the present invention predicted to contain oil. All of the dry and wet holes 30c, 30d, 30e, 30f, 30g, 30i, 30j, 30m are positioned in areas 240 that an event contrast stacker 64 in accordance with the present invention predicted not to contain oil. Additionally, other areas 242 are illustrated to indicate where future wells 30 may be drilled with a high likelihood of finding extractable oil.

EXAMPLE II

Referring to FIGS. 44–49, in the present example, traces (post-stack gathers) were collected from an eight square mile area of an operating gas field. The data was used to form the conventional seismic volume illustrated in FIG. 47. Five wells 30 were drilled based on that seismic volume. As can be seen, all the wells 30 are positioned in areas 234 that the seismic volume indicated as likely locations for gas.

Of the five wells 30, well one 30a resulted in a gas well and well two 30b resulted in non-producing wet hole (producing water not gas). The states of the remaining three wells 30c, 39d, 30e were known to the owners of the gas field, but were withheld until completion of processing in accordance with the present invention.

As illustrated in FIG. 44, selected signals 24 corresponding to each of the wells 30 were provided for processing. The number 236 of signals 24 provided for each well 30 ranged from 431 to 606. The signals 24 were processed by an event contrast stacker 64 in accordance with the present invention.

The area of interest, or pay horizon 62, of the gas field of the present example was located about 0.85 seconds from the surface 16. In a first application of an event contrast stacker 64 in accordance with the present invention, an epoch 68 was taken from each of the signals 24 in the range extending from 0.1 seconds before the pay horizon 62 to 0.1 seconds after the pay horizon 62. Thus, each epoch 68 of the first application represented 0.2 seconds (200 milliseconds) of a signal 24. Thus, the epochs 68 corresponding to the wells 30 extended from approximately time 0.75 to time 0.95.

In a second application of an event contrast stacker 64 in accordance with the present invention, an epoch 68 was taken from each of the signals 24 in the range extending from 0.04 seconds before the pay horizon 62 to 0.04 seconds after the pay horizon 62. Thus, each epoch 68 of the first application represented 0.080 seconds (80 milliseconds) of a signal 24. Thus, the epochs 68 corresponding to the wells 30 extended from approximately time 0.81 to time 0.89.

The geological formation 19 containing well one 30a, a gas well, was considered an example of state A (i.e. a gas-producing location). The geological formation 19 containing well two 30b, a wet hole, was considered an example of state B (i.e. a non-gas-producing location). Epochs 68 corresponding to wells one 30a and two 30b were used as learning epochs 72 and processed by a learning system 76 in accordance with the present invention. Epochs 68 corresponding to wells three 30c, four 30d, and five 30e were used as classification epochs 74 and processed by a classification system 78 in accordance with the present invention.

After processing the learning epochs 72 corresponding to the 200 millisecond time window, the learning system 76 produced a separation key 80a illustrated in part by FIG. 45. It was determined that each epoch 72 may be weighted in time space with a Gaussian distribution 102 centered at a time of 40 milliseconds (halfway though the epoch 72) with a time width 106 of 40 milliseconds. It was also determined that each epoch 72 may be divided in frequency space into five frequency bands 100. The frequency bands 100 may be weighted with a Gaussian distribution 102s centered at 25 Hz, 50 Hz, 75 Hz, 100 Hz, and 120 Hz, all with frequency widths 110 of 5 Hz. Weights 122 for the resulting feature segments 92 may be applied as illustrated.

After processing the learning epochs 72 corresponding to the 80 millisecond time window, the learning system 76 produced a separation key 80b illustrated in part by FIG. 46. It was determined that each epoch 72 may be weighted in time space with a Gaussian distribution 102 centered at time 100 milliseconds (halfway though the epoch 72) with a time width 106 of 100 milliseconds. It was also determined that each epoch 72 may be divided in frequency space into three frequency bands 100. The frequency bands 100 may be weighted with Gaussian distributions 102 centered at 9.09 Hz, 18.18 Hz, and 27.27 Hz, all with frequency widths 110 of 15 Hz. Weights 122 for the resulting feature segments 92 may be applied as illustrated.

The learning epochs 72 and the classification epochs 74 corresponding to the first and second applications were processed by the classification system 78 using the respective separation keys 80a, 80b developed by the learning system 76. For both applications, each epoch 68 was expanded into feature segments 92. The feature segments 92 corresponding to a particular epoch 68 were weighted, superimposed 128, and aggregated 130 to a numerical value. From the resulting data, an output generator 82 in accordance with the present invention generated respective vertical, two-dimensional slices 212a, 212b.

As seen in FIGS. 47 and 48, in both the first and second applications, well one 30a was properly positioned in an area 238 classified as gas producing and well two 30b was properly positioned in an area 240 classified as non gas producing. Additionally, other presently untapped areas 242 were classified as likely to be gas producing. Of the unknown, test wells (i.e. wells three 30c, four 30d, and five 30e), wells four 30d and five 30e were classified as gas wells, while well three 30c was classified as a non-producing well. Upon viewing the data, the gas field owners confirmed that wells four 30d and five 30e were indeed gas wells and well three 30c was indeed a non-producing well. Thus, the processing of the event contrast stacker 64 in accordance with the present invention was validated.

EXAMPLE III

Figure 50:
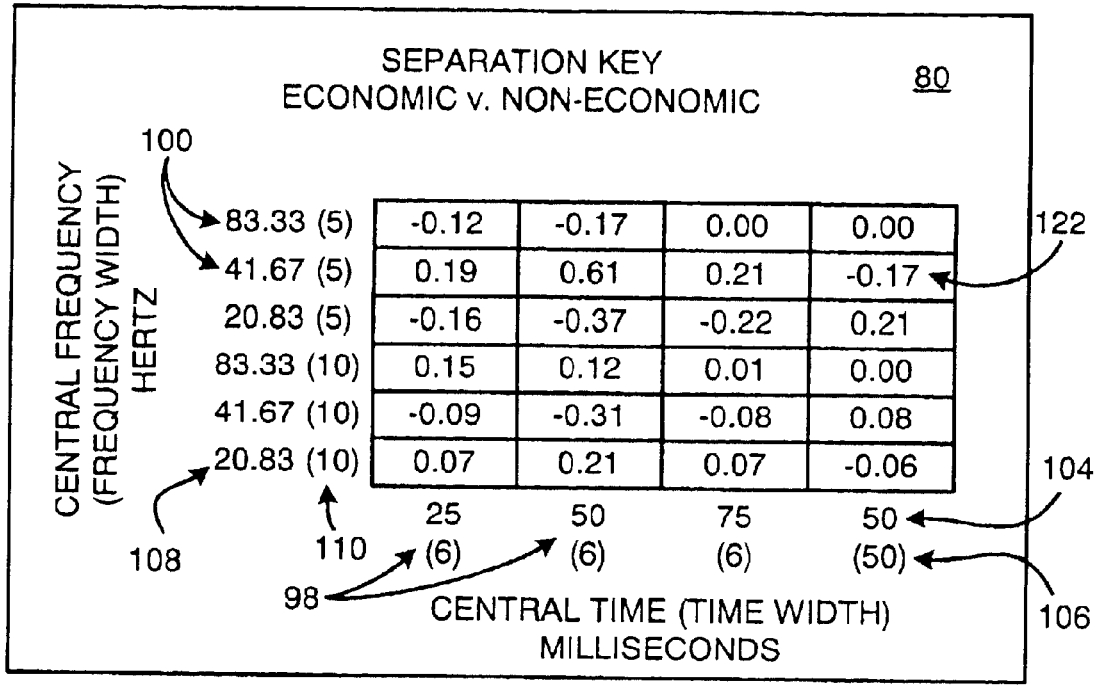
FIG. 50 is a table illustrating a portion of a separation key found by an event contrast stacker in accordance with the present invention to be effective in segregating seismic data pertaining to gas production above a selected economic value from seismic data pertaining to gas production below a selected economic value.

Referring to FIG. 50, in the present example, signal 24 was provided from a first geological formation 19 having gas production rates above a selected economic value and a geological formation 19 having gas production rates below a selected economic value. Epochs 68 corresponding to the first and second geological formations 19 were used as learning epochs 72 and processed by a learning system 76 in accordance with the present invention.

After processing, the learning system 76 produced a separation key 80 effective to separate geological formations 19 having gas production above a selected value from geological formations 19 having gas production below a selected value. The separation key 80, illustrated in part in FIG. 50, instructs that each epoch 72 be divided in both time and frequency space. In time space, each epoch 72 may be divided into four time segments 98. The time segments 98 may be weighted with Gaussian distributions 102 centered at 25 ms, 50 ms, 75 ms, and 50 ms. The time segments may have time widths 106 of 6 ms, 6 ms, 6 ms, and 50 ms, respectively.

In frequency space, each epoch 72 may be divided into six frequency bands 100. The frequency bands 100 may be weighted with Gaussian distributions 102 centered at 20.83 Hz, 41.67 Hz, and 83.33 Hz, all with frequency widths 110 of 10 Hz, and at 20.83 Hz, 41.67 Hz, and 83.33 Hz, all with frequency widths 110 of 5 Hz. Weights 122 for the resulting feature segments 92 may be applied as illustrated.

EXAMPLE IV

Figure 51:
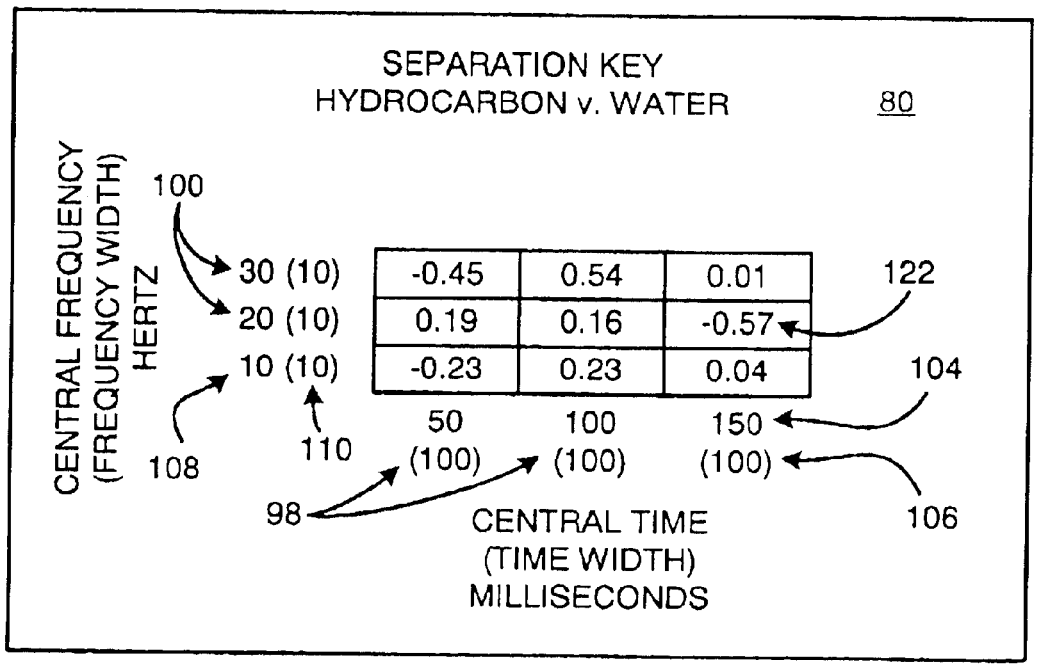
FIG. 51 is a table illustrating a portion of a separation key found by an event contrast stacker in accordance with the present invention to be effective in segregating seismic data pertaining to hydrocarbon deposits from seismic data pertaining to water deposits.

Referring to FIG. 51, in the present example, signal 24 was provided from a first collection of geological formations 19 producing hydrocarbons (i.e. gas, oil, or gas and oil) and a second collection of geological formations 19 producing water. Epochs 68 corresponding to the first and second collections were used as learning epochs 72 and processed by a learning system 76 in accordance with the present invention.

After processing, the learning system 76 produced a separation key 80 effective to separate geological formations 19 producing a hydrocarbon from geological formations 19 producing water. The separation key 80, illustrated in part in FIG. 51, instructs that each epoch 72 be divided in both time and frequency space. In time space, each epoch 72 may be divided into three time segments 98. The time segments 98 may be weighted with Gaussian distributions 102 centered at 50 ms, 100 ms, and 150 ms, all with time widths 106 of 100 ms. In frequency space, each epoch 72 may be divided into three frequency bands 100. The frequency bands 100 may be weighted with Gaussian distributions 102 centered at 10 Hz, 20 Hz, and 30 Hz, all with frequency widths 110 of 10 Hz. Weights 122 for the resulting feature segments 92 may be applied as illustrated.

From the above discussion, it will be appreciated that the present invention provides an integrated waveform analysis method and apparatus capable of extracting useful information from highly complex, irregular, and seemingly random or simply noise-type waveforms such as seismic traces and well log data. Unlike prior art devices, the present invention provides novel systems and methods for signal processing, pattern recognition, and data interpretation by means of observing and correlating the affects of a particular state on a geological formation.

The present invention may be embodied in other specific forms without departing from its essential characteristics. The described embodiments are to be considered in all respects only as illustrative, and not restrictive. The scope of the invention is, therefore, indicated by the appended claims, rather than by the foregoing description. All changes within the meaning and range of equivalency of the claims are to be embraced within their scope.

What is claimed and desired to be secured by United States Letters Patent is:

1. A method comprising:
   providing a first signal segment corresponding to a first geological formation having a first characteristic;
   providing a second signal segment corresponding to a second geological formation having a second characteristic, distinct from the first characteristic;
   expanding the first and second signal segments in at least one of frequency space and time space by applying at least one feature operator to the first and second signal segments to generate a plurality of first feature segments corresponding to the first signal segment and a plurality of second feature segments corresponding to the second signal segment;
   weighting the pluralities of first and second feature segments by applying a weight table to the pluralities of first and second feature segments to generate a weighted plurality of first feature segments and a weighted plurality of second feature segments, respectively; and
   collapsing the weighted plurality of first feature segments to form a first feature comprising a non-random first pattern and the weighted plurality of second feature segments to form a second feature having a second pattern distinct from the non-random first pattern.

2. The method of claim 1, further comprising generating a separation key listing the at least one feature operator used to expand the first and second signal segments and the weighting table applied to the pluralities of first and second feature segments.

3. The method of claim 2, further comprising providing a third signal segment corresponding to a third geological formation.

4. The method of claim 3, further comprising expanding, weighting, and collapsing the third signal segment in accordance with the at least one feature operator and weighting table listed in the separation key to generate a third feature.

5. The method of claim 4, further comprising classifying the third geological formation as having one of the first and second characteristics based on the correspondence of the third feature to one of the first feature and the second feature.

6. The method of claim 5, wherein the first characteristic is selected from the group consisting of porosity above a first threshold value, density above a second threshold value, pressure above a third threshold value, shale in a concentration above a fourth threshold value, hydrocarbon production above a fifth threshold value, temperature above a sixth threshold value, and sand in a concentration above a seventh threshold value.

7. The method of claim 6, wherein the second characteristic is selected from the group consisting of porosity below the first threshold value, density below the second threshold value, pressure below the third threshold value, shale in a concentration below the fourth threshold value, hydrocarbon production below the fifth threshold value, temperature below the sixth threshold value, and sand in a concentration below the seventh threshold value.

8. The method of claim 1, wherein the first signal segment is a portion of a seismic trace.

9. The method of claim 8, wherein a dominant waveform exists in the first signal segment and is an apparently substantially random waveform.

10. The method of claim 9, wherein the dominant waveform of the first signal segment effectively obscures other waveforms.

11. The method of claim 10, wherein weighting comprises applying weights selected based on their effectiveness to neutralize the random contribution of the dominant waveform.

12. The method of claim 1, wherein expanding comprises dividing the first and second signal segments into selected frequency bands.

13. The method of claim 12, wherein a first feature operator of the at least one feature operator provides selected central frequencies and corresponding frequency widths to define the boundaries of the selected frequency bands.

14. The method of claim 12, wherein expanding comprises dividing the first and second signal segments into selected time segments and wherein a second feature operator of the at least one feature operator provides selected central times and corresponding times widths to define the boundaries of the selected time segments.

15. The method of claim 14, wherein collapsing comprises superimposing the weighted plurality of first feature segments to form a first feature comprising a non-random first pattern and the weighted plurality of second feature segments to form a second feature having a second pattern distinct from the non-random first pattern.

16. A method comprising:
   providing a first signal corresponding to a first geological formation tapped by a hydrocarbon well producing hydrocarbons above a threshold rate;
   providing a second signal corresponding to a second geological formation tapped by a hydrocarbon well producing hydrocarbons below the threshold rate;
   expanding the first and second signal segments in at least one of frequency space and time space by applying at least one feature operator to the first and second signal segments to generate a plurality of first feature segments corresponding to the first signal segment and a plurality of second feature segments corresponding to the second signal segment;

weighting the pluralities of first and second feature segments by applying a weight table to the pluralities of first and second feature segments to generate a weighted plurality of first feature segments and a weighted plurality of second feature segments, respectively;

superimposing the weighted plurality of first feature segments to form a first feature comprising a non-random first pattern and the weighted plurality of second feature segments to form a second feature having a second pattern distinct from the non-random first pattern; and generating a separation key listing the at least one feature operator used to expand the first and second signal segments and the weighting table applied to the pluralities of first and second feature segments.

17. The method of claim 16, wherein the first signal is a pre-stack, migrated seismic trace.

18. The method of claim 17, wherein the second seismic trace is a pre-stack, migrated seismic trace.

19. The method of claim 16, wherein the first seismic trace is a post-stack, migrated seismic trace.

20. The method of claim 19, wherein the second seismic trace is a post-stack, migrated seismic trace.

21. The method of claim 16, wherein the hydrocarbon well is an oil well.

22. The method of claim 16, wherein the hydrocarbon well is a gas well.

23. The method of claim 16, wherein expanding comprises dividing the first and second signal segments into selected frequency bands and wherein a first feature operator of the at least one feature operator provides selected central frequencies and corresponding frequency widths to define the boundaries of the selected frequency bands.

24. The method of claim 23, wherein the first feature operator imposes a Gaussian weighting at centered at each of the selected central frequencies to define the selected frequencies bands.

25. The method of claim 23, wherein expanding comprises dividing the first and second signal segments into selected time segments and wherein a second feature operator of the at least one feature operator provides selected central times and corresponding times widths to define the boundaries of the selected time segments.

26. The method of claim 25, wherein the second feature operator imposes a Gaussian weighting centered at each of the selected central times to define the selected time segments.

27. The method of claim 23, wherein collapsing comprises superimposing the weighted plurality of first feature segments to form a first feature comprising a non-random first pattern and the weighted plurality of second feature segments to form a second feature having a second pattern distinct from the non-random first pattern.

28. The method of claim 27, further comprising providing a third signal corresponding to a third geological formation containing a prospective hydrocarbon well location.

29. The method of claim 28, further comprising processing third signal in accordance with the at least one feature operator and weighting table listed in the separation key to produce a third feature.

30. The method of claim 29, further comprising classifying the prospective hydrocarbon well location as one of hydrocarbon well producing above the threshold rate and a hydrocarbon well producing below the threshold rate based on the correspondence of the third feature to one of the first feature and the second feature.

31. A method for predicting the state of a geological formation, the method comprising:

providing a separation key effective to extract a first feature from a signal corresponding to a first state and a second feature, distinct from the first feature, from a signal corresponding to a second state, the separation key listing at least one feature operator and a weighting table;

providing a first test signal collected from the geological formation;

applying the at least one feature operator to expand the first test signal in at least one of frequency space and time space to generate a plurality of feature segments;

generating a weighted plurality of feature segments by applying the weighting table to the plurality of feature segments;

collapsing the weighted plurality of feature segments to generate a third feature; and classifying the geological formation as having one of the first state and second state based on the correspondence of the third feature to one of the first feature and second feature.

32. The method of claim 31, further comprising providing a second test signal collected from the geological formation at a time after the first test signal was collected.

33. The method of claim 32, further comprising processing the second test signal by applying the at least one feature operator, applying the weight table, and collapsing to generate a forth feature.

34. The method of claim 33, further comprising quantifying changes in the geological formation between the time the first test signal was collected and the time the second test signal was collected by comparing the fourth feature to the first feature.

35. The method of claim 31, further comprising selecting a color spectrum comprising at least two colors and having a first extreme and a second extreme, opposite the first extreme, and assigning the color of the first extreme to the first feature and the color of the second extreme to the second feature.

36. The method of claim 35, further comprising assigning the third feature a color selected from the color spectrum based on the relative correspondence of the third feature to the first and second features.

37. The method of claim 36, further comprising providing a plurality of test signals, each collected from a different location on the geological formation.

38. The method of claim 37, further comprising processing the plurality of test signals by applying the at least one feature operator, applying the weight table, and collapsing to generate a plurality of features.

39. The method of claim 38, further comprising assigning each of the plurality of features a color selected from the color spectrum based on the relative correspondence thereof to the first and second features.

40. The method of claim 39, further comprising generating a two-dimensional image of the geological formation by coloring portions of the image in accordance with the color assigned to the feature of the plurality of features corresponding to the portions.

41. A method for predicting the presence of extractable hydrocarbons in a geological formation, the method comprising:

providing a separation key effective to extract a first feature from signal collected from a first geological formation tapped by a hydrocarbon well producing above a threshold rate and a second feature from signal collected from a second geological formation tapped by a hydrocarbon well producing below the threshold rate, the separation key listing at least one feature operator and a weighting table;

providing a test signal collected from a third geological formation;

applying the at least one feature operator to expand the test signal in at least one of frequency space and time space to generate a plurality of feature segments;

generating a weighted plurality of feature segments by applying the weighting table to the plurality of feature segments;

superimposing the weighted plurality of feature segments to generate a third feature; and classifying the third geological formation as one of producing hydrocarbons above the threshold rate and producing hydrocarbons below the threshold rate based on the correspondence of the third feature to one of the first feature and second feature.

* * * * *

UNITED STATES PATENT AND TRADEMARK OFFICE
CERTIFICATE OF CORRECTION

| | | |
|---|---|---|
| PATENT NO. | : 6,952,649 B2 | Page 1 of 1 |
| APPLICATION NO. | : 10/676945 | |
| DATED | : October 4, 2005 | |
| INVENTOR(S) | : Cook et al. | |

It is certified that error appears in the above-identified patent and that said Letters Patent is hereby corrected as shown below:

Column 1, line 6, the recitation of priority should read --This application: claims the benefit of U.S. Provisional Application Serial No. 60/416,342, filed October 4, 2002; and is a continuation-in-part of co-pending U.S. Patent Application Serial No. 10/364,785, filed February 11, 2003, which is a continuation of U.S. Patent Application Serial No.08/840,052, filed April 24, 1997.--.

Column 3, line 13, "though" should be changed to --thought--.

Column 17, line 28, "a epoch" should be changed to --an epoch--.

Column 18, line 44, "divided" should be changed to --divide--.

Signed and Sealed this

Twenty-ninth Day of May, 2007

JON W. DUDAS
*Director of the United States Patent and Trademark Office*